(12) United States Patent
Saito et al.

(10) Patent No.: US 9,759,681 B2
(45) Date of Patent: Sep. 12, 2017

(54) BIOMOLECULE DETECTION METHOD, BIOMOLECULE DETECTION DEVICE AND ANALYSIS DEVICE

(71) Applicant: Hitachi High-Technologies Corporation, Tokyo (JP)

(72) Inventors: Toshiro Saito, Tokyo (JP); Kenta Imai, Tokyo (JP); Kyoko Imai, Tokyo (JP); Kazumichi Imai, Tokyo (JP); Itaru Yanagi, Tokyo (JP); Yoshimitsu Yanagawa, Tokyo (JP); Masahiko Ando, Tokyo (JP); Naoshi Itabashi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 77 days.

(21) Appl. No.: 14/418,480

(22) PCT Filed: Jun. 28, 2013

(86) PCT No.: PCT/JP2013/067755
§ 371 (c)(1),
(2) Date: Jan. 30, 2015

(87) PCT Pub. No.: WO2014/024598
PCT Pub. Date: Feb. 13, 2014

(65) Prior Publication Data
US 2015/0308977 A1   Oct. 29, 2015

(30) Foreign Application Priority Data
Aug. 8, 2012   (JP) ................................. 2012-175572

(51) Int. Cl.
*G01N 27/414*   (2006.01)
*G01N 33/487*   (2006.01)
(Continued)

(52) U.S. Cl.
CPC ..... *G01N 27/4145* (2013.01); *G01N 27/4148* (2013.01); *G01N 33/48721* (2013.01);
(Continued)

(58) Field of Classification Search
CPC ......... G01N 27/4145; G01N 33/48721; G01N 37/00; G01N 27/4148; G01N 33/543
See application file for complete search history.

(56) References Cited

U.S. PATENT DOCUMENTS 8,796,040 B2   8/2014  Aizawa et al.
2003/0211502 A1*  11/2003  Sauer .................. C12Q 1/6869
                                                          435/6.11
(Continued)

FOREIGN PATENT DOCUMENTS

JP   2005-304376   4/2005
JP   47-48542      5/2011
(Continued)

OTHER PUBLICATIONS

Pothur R. Srinivas et al., Trends in biomarker research for cancer detection, Lancet Oncol. vol. 2, Nov. 2001, pp. 698-704.
(Continued)

*Primary Examiner* — Melanie Y Brown
(74) *Attorney, Agent, or Firm* — Mattingly & Malur, PC

(57) ABSTRACT

The present invention is intended to provide a method and a device for detecting a biomolecule with high sensitivity and high throughput over a wide dynamic range without requiring concentration adjustments of a sample in advance. The present invention specifically binds charge carriers to a detection target biomolecule, and detects the detection target biomolecule one by one by measuring a current change that occurs as the conjugate of the biomolecule and the charge
(Continued)

carriers passes through a micropore. High-throughput detection of a biomolecule sample is possible with an array of detectors.

5 Claims, 23 Drawing Sheets

(51) Int. Cl.
*G01N 33/543* (2006.01)
*G01N 37/00* (2006.01)

(52) U.S. Cl.
CPC ..... *G01N 33/543* (2013.01); *G01N 33/54306* (2013.01); *G01N 37/00* (2013.01)

(56) References Cited

U.S. PATENT DOCUMENTS

| | | | |
|---|---|---|---|
| 2005/0148101 A1* | 7/2005 | Bamdad | B82Y 5/00 436/524 |
| 2008/0050752 A1 | 2/2008 | Sun et al. | |
| 2009/0136958 A1 | 5/2009 | Gershow et al. | |
| 2010/0066348 A1* | 3/2010 | Merz | C12Q 1/6869 324/71.1 |
| 2010/0143887 A1 | 6/2010 | Kim et al. | |
| 2010/0327847 A1 | 12/2010 | Leiber et al. | |
| 2010/0327874 A1* | 12/2010 | Liu | G01N 33/48721 324/464 |
| 2011/0133255 A1 | 6/2011 | Merz | |
| 2011/0237000 A1 | 9/2011 | Tey et al. | |
| 2011/0308950 A1 | 12/2011 | Sakai et al. | |
| 2012/0312083 A1 | 12/2012 | Akahori et al. | |

FOREIGN PATENT DOCUMENTS

| | | |
|---|---|---|
| JP | 2012-026986 | 2/2012 |
| WO | 01/81896 | 11/2001 |

OTHER PUBLICATIONS

Douglas Galasko, Biomarkers for Alzheimer's disease, J. Alzheimers Dis. 8, (2005), pp. 339-346.

Janet M. Barletta et al., Lowering the Detection Limits of HIV-1 Viral Load Using Real-Time Immuno-PCR for HIV-1 p24 Antigen, Am J Clin Pathol 2004; 122:20-27.

David A. Giljohann et al., Drivers of Biodiagnostic Development, Nature 462, 461-464 (2009).

David M. Rissin et al., Single-molecule enzyme-linked immunosorbent assay detects serum proteins at subfemtomolar concentrations, Nature Biotechnology, 28, 1641 (2010).

Daniel Fologea et al., Electrical characterization of protein molecules by a solid-state nanopore, Appl Phys Lett., 91, 053901-3 (2007).

M.S. Romero-Cano et al., Colloidal stabilization of polystyrene particles by adsorption of nonionic surfactants, Journal of Colloid and Interface Science, 198, 266-272 (1998).

\* cited by examiner

[FIG. 1]
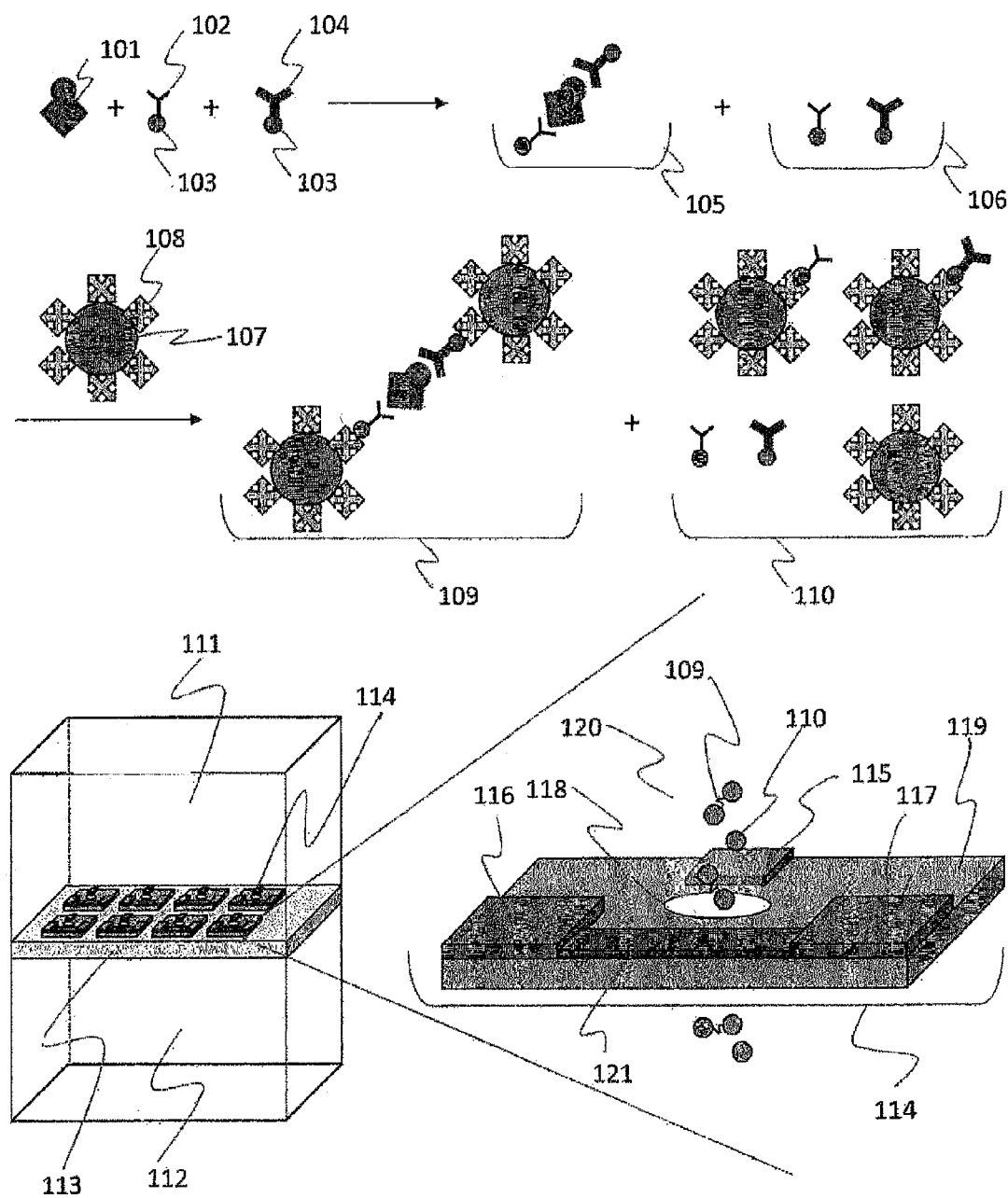

[FIG. 2]

[FIG. 3]
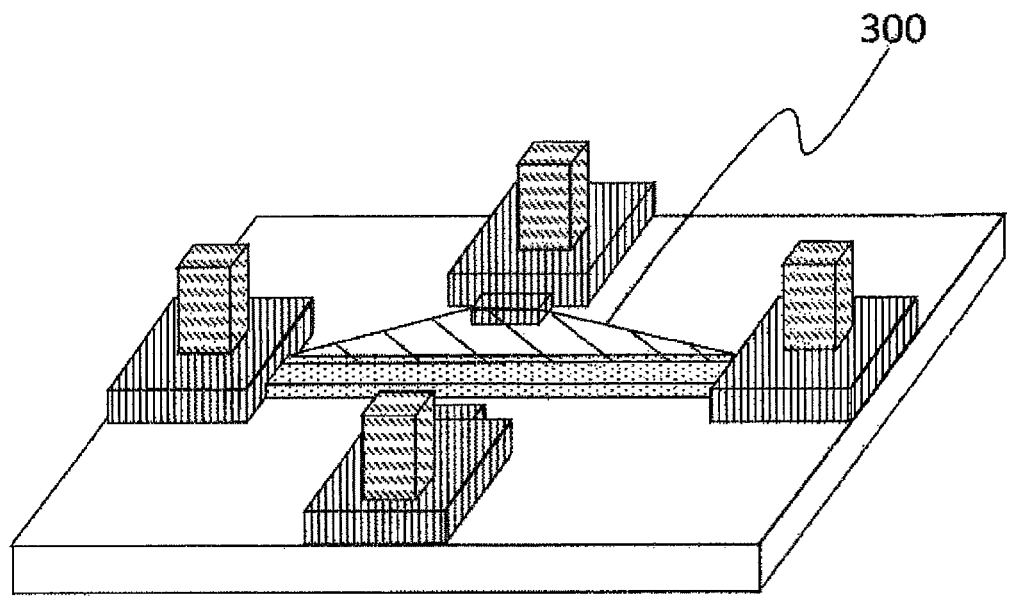

[FIG. 4]
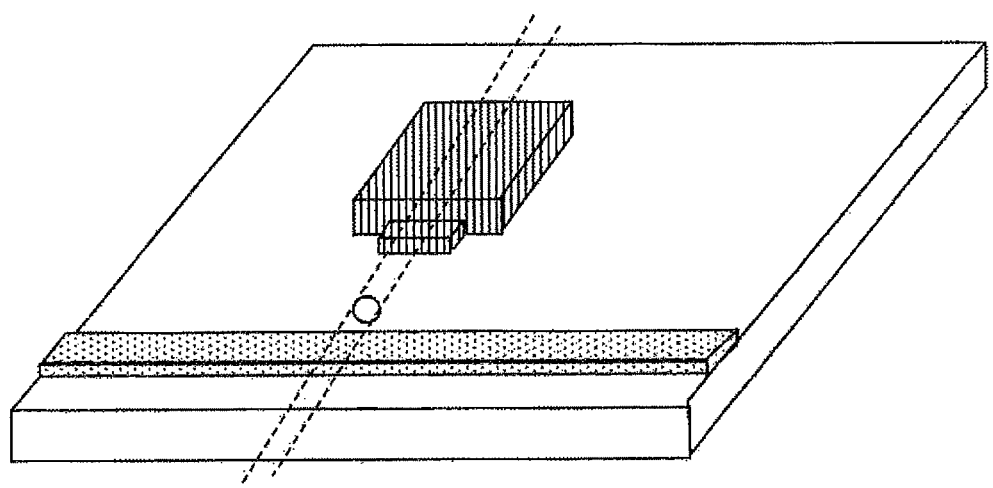
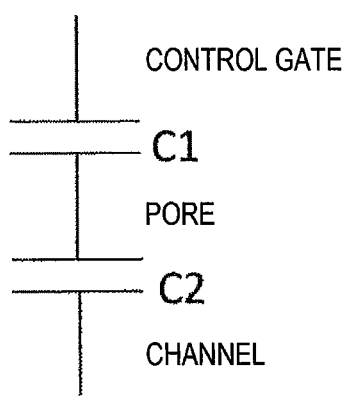

[FIG. 5]
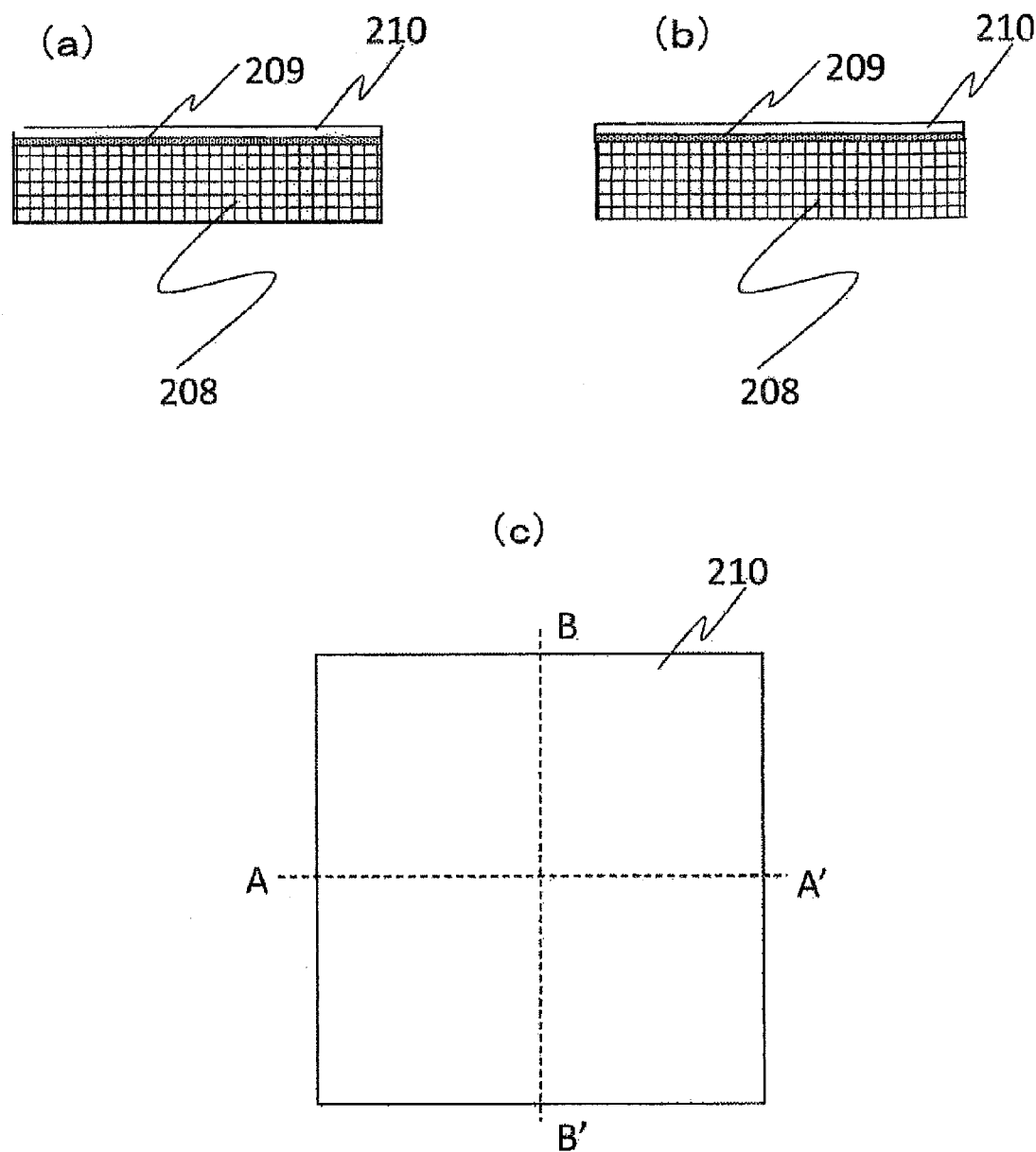

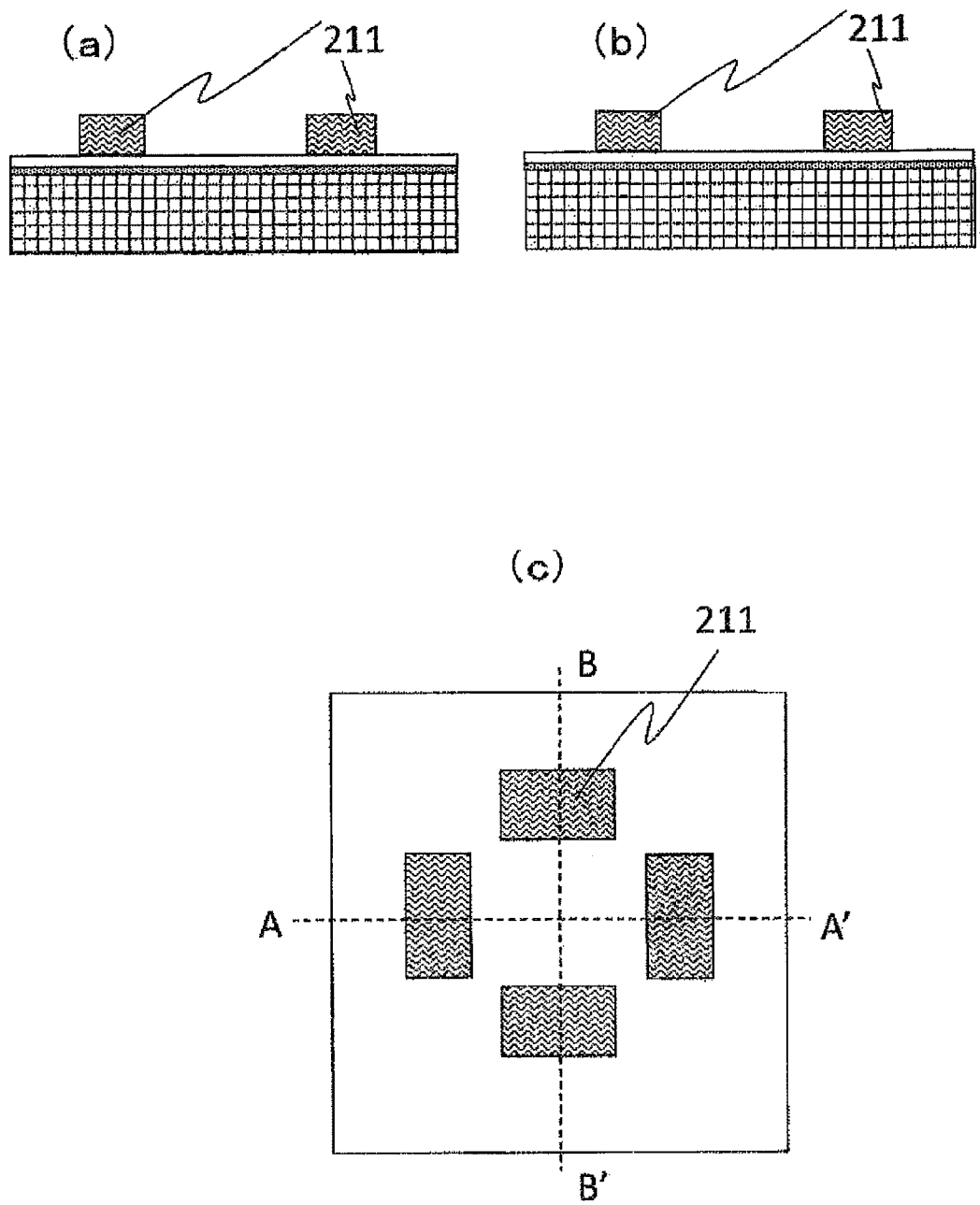
[FIG. 6]

[FIG. 7]
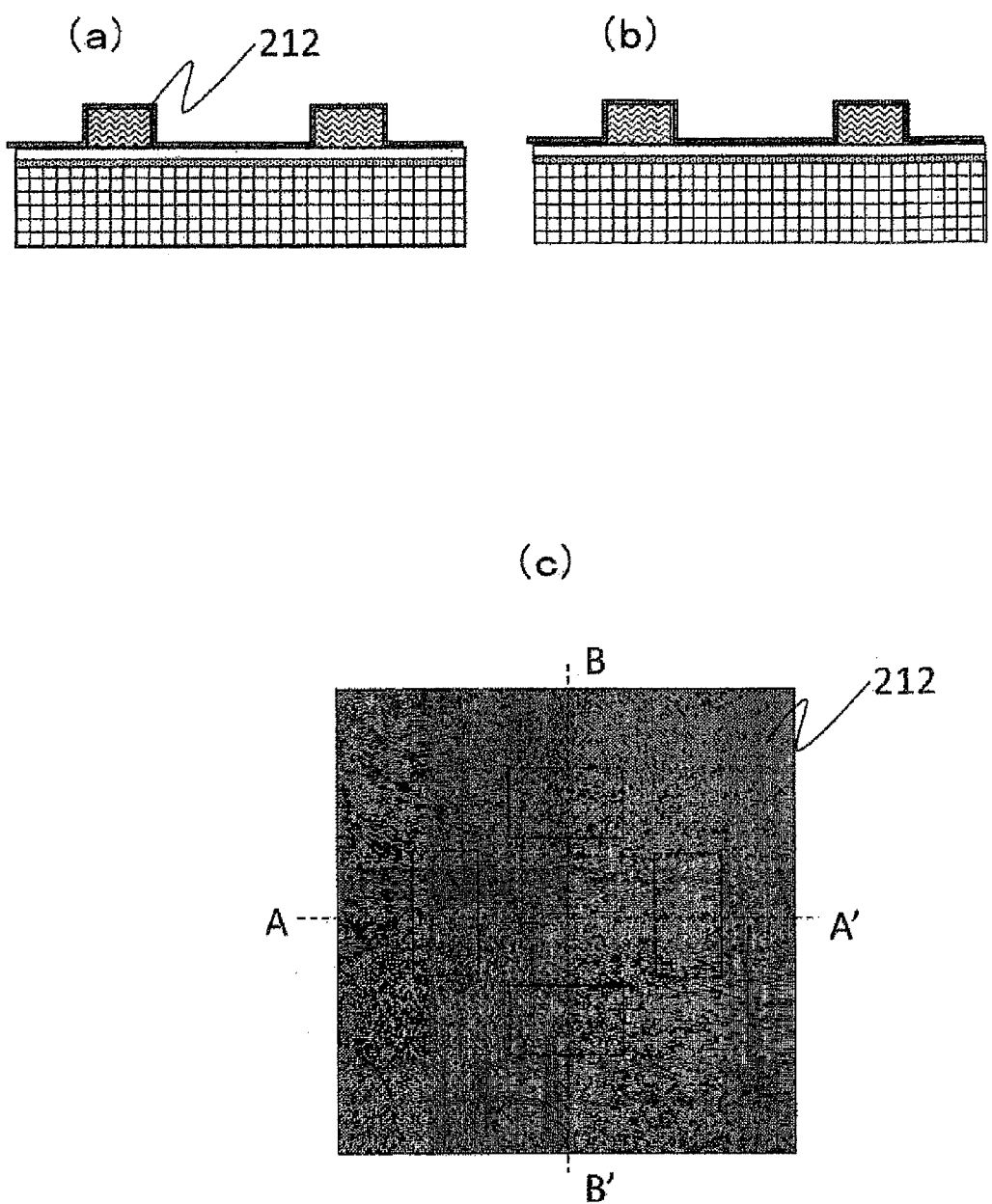

[FIG. 8]
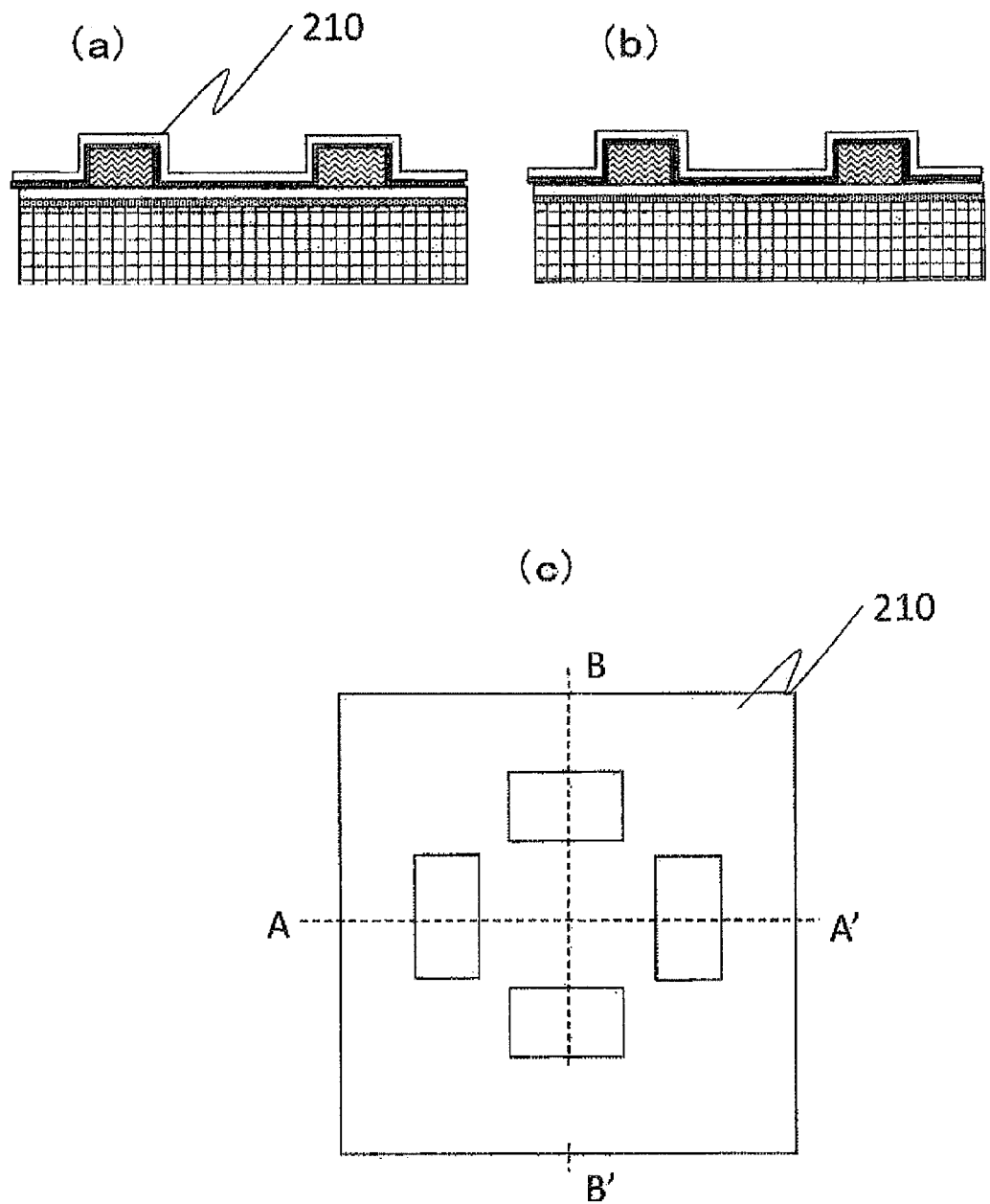

[FIG. 9]
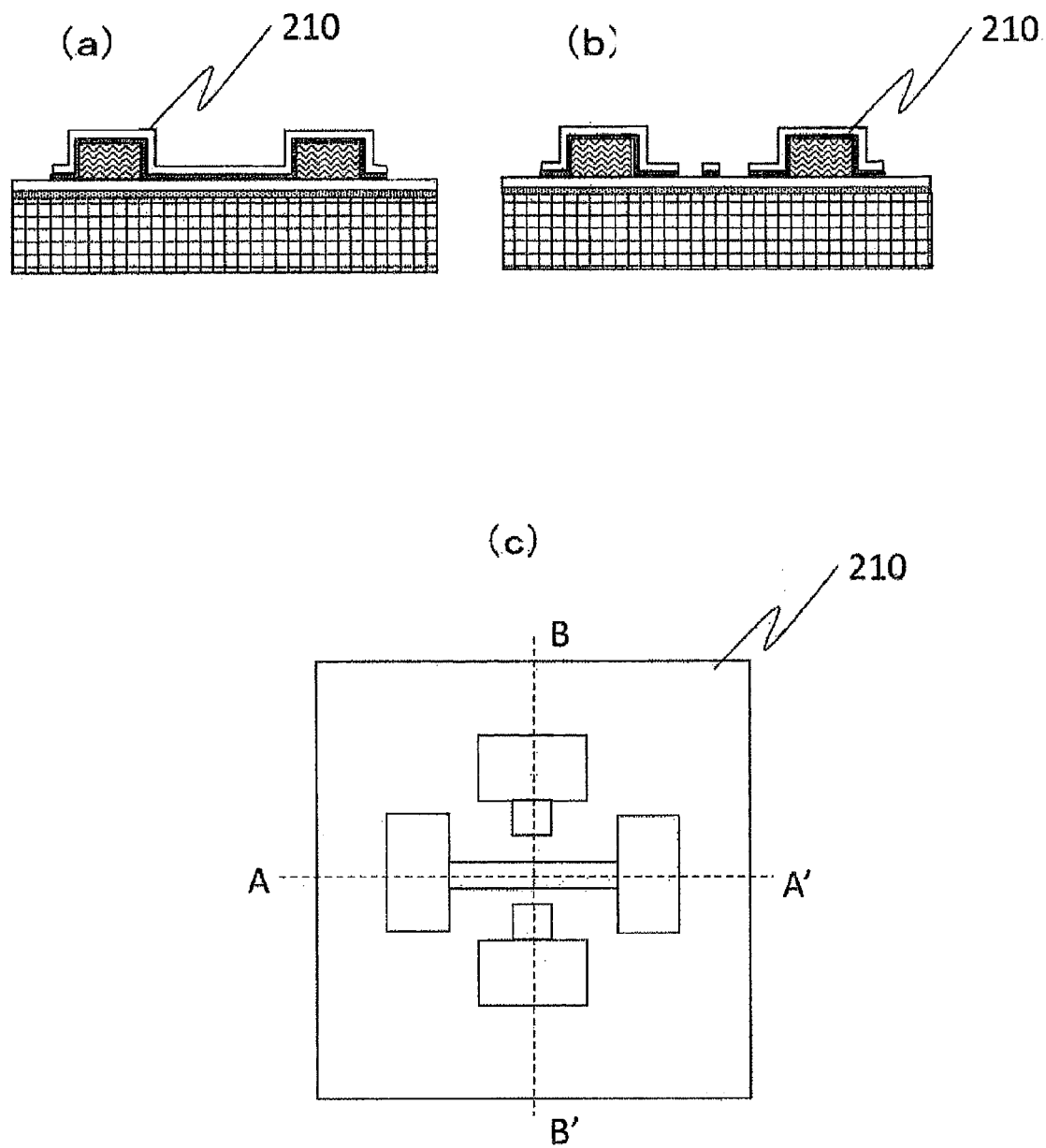

[FIG. 10]
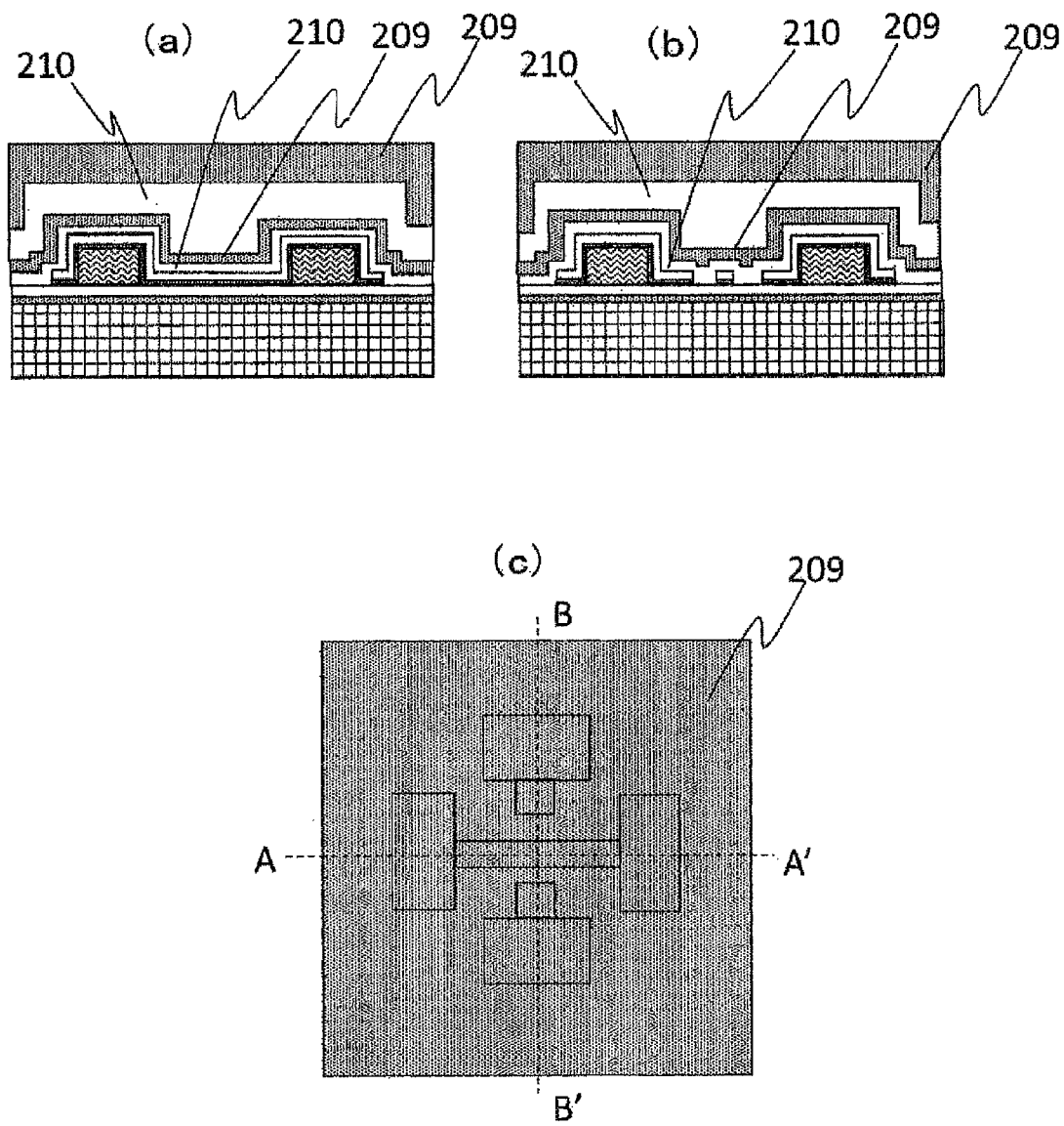

[FIG. 11]
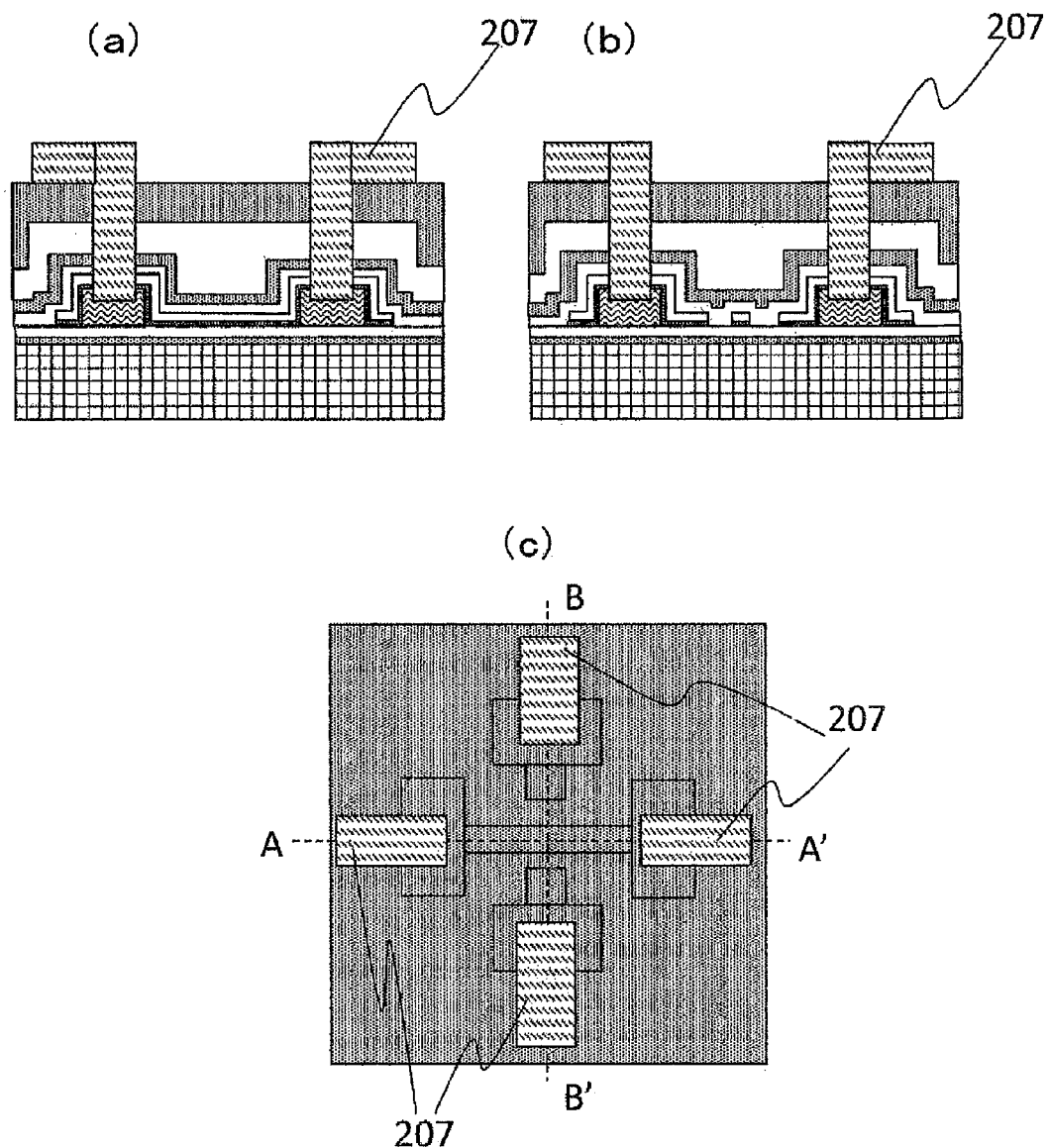

[FIG. 12]
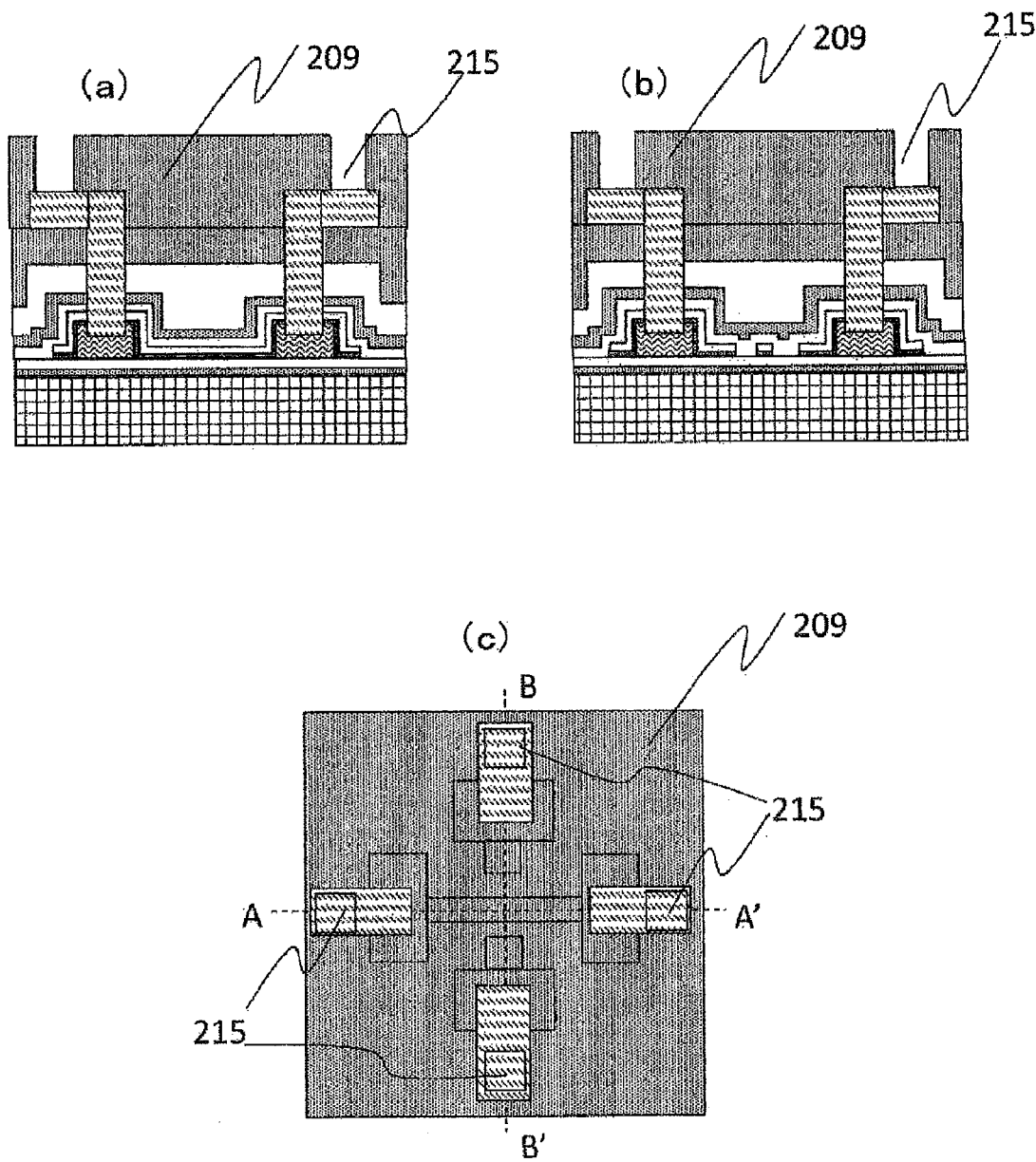

[FIG. 13]
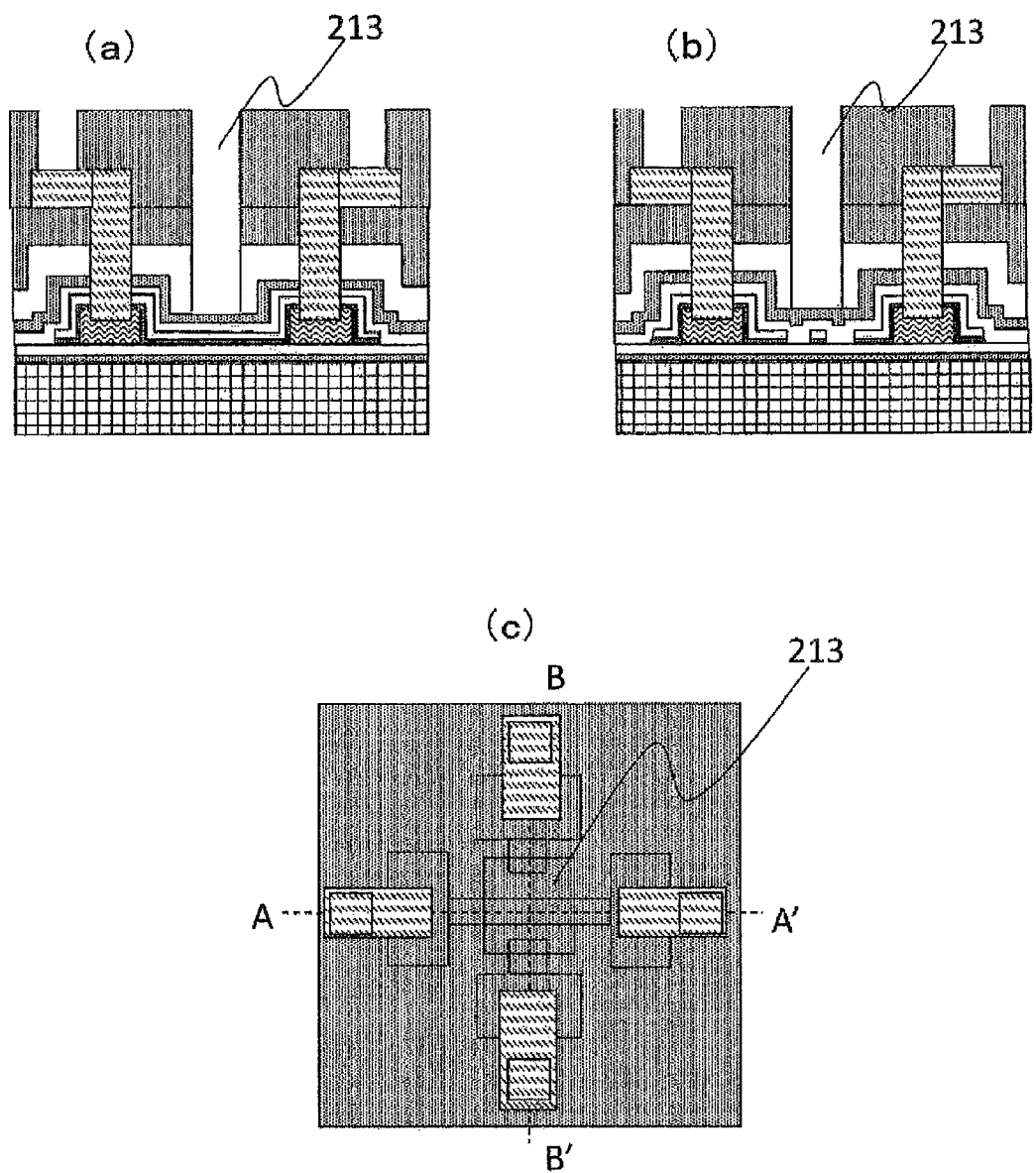

[FIG. 14]
(a)
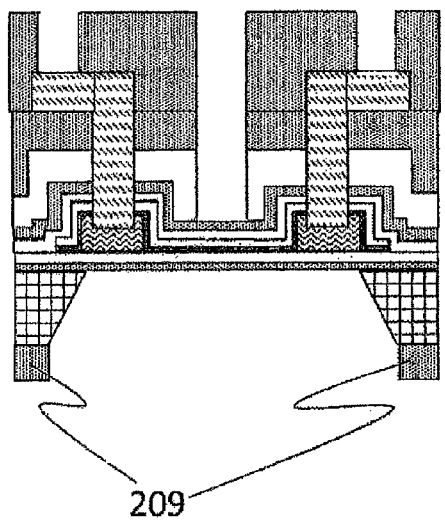
209
(b)
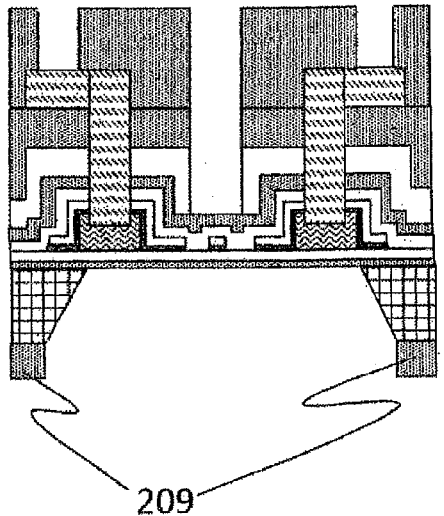
209
(c)
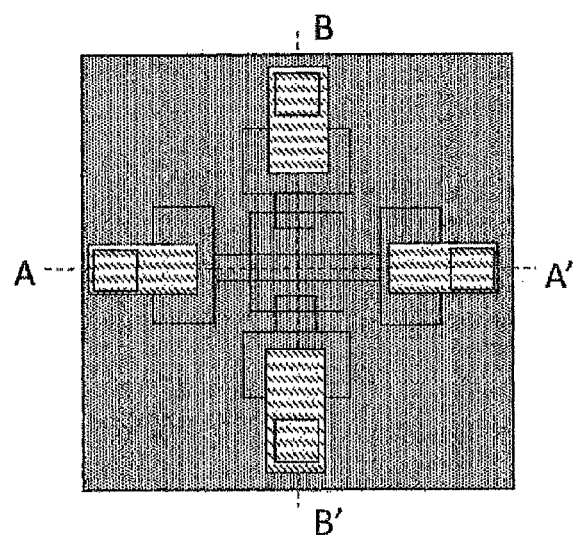

FIG. 15]
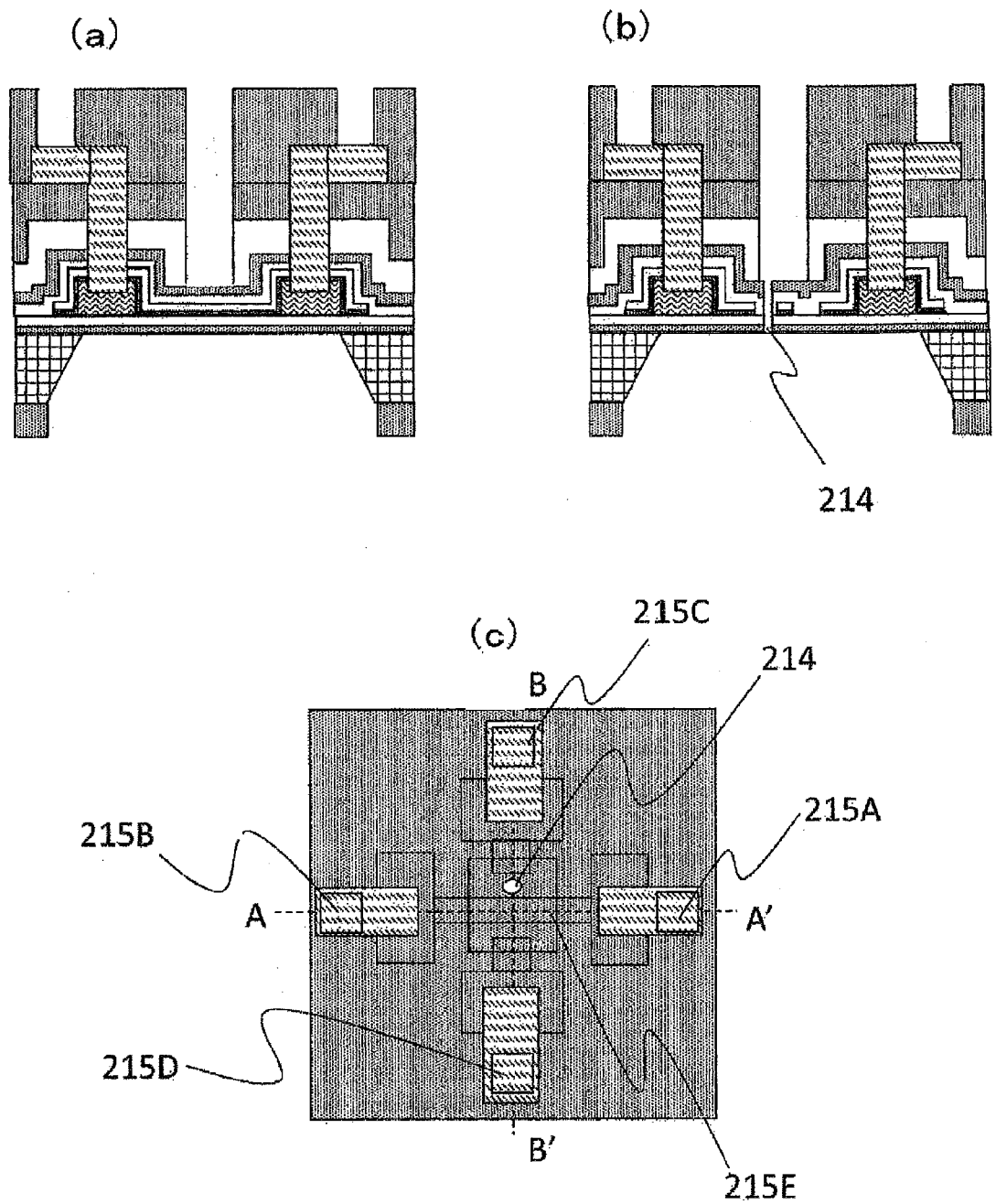

[FIG. 16]
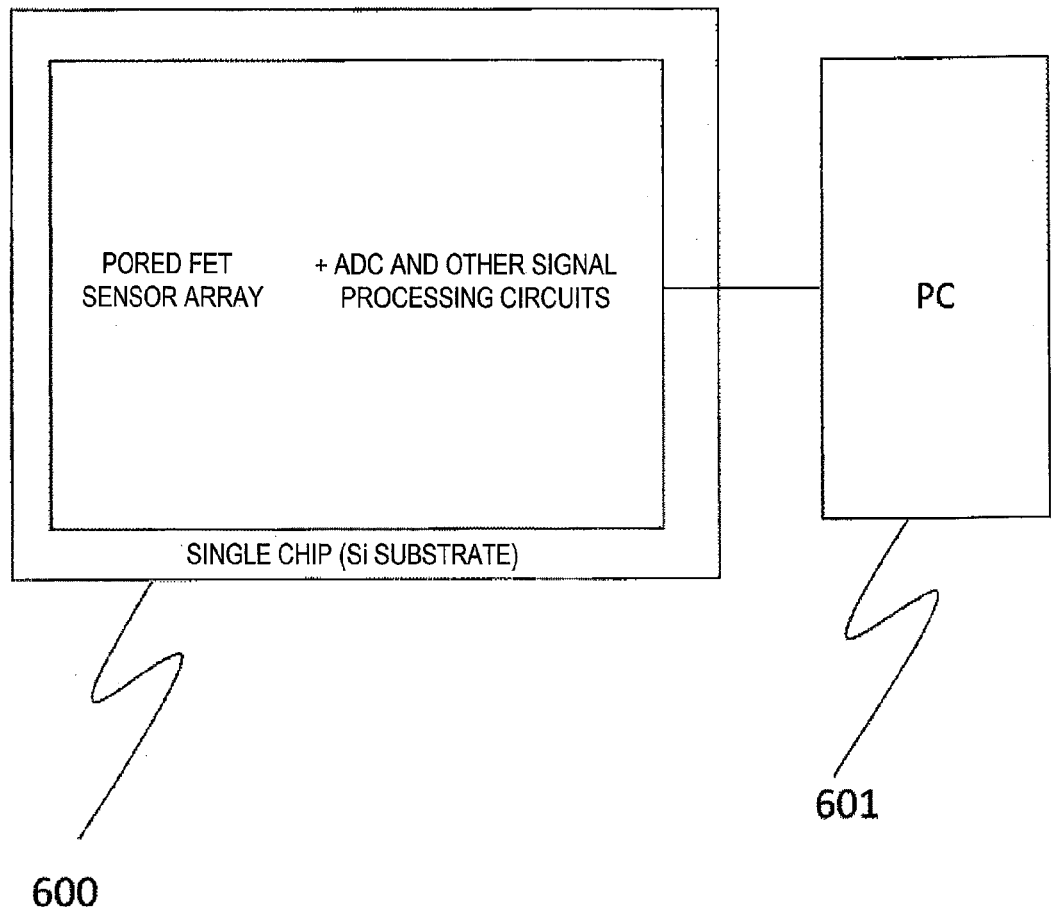

[FIG. 17]
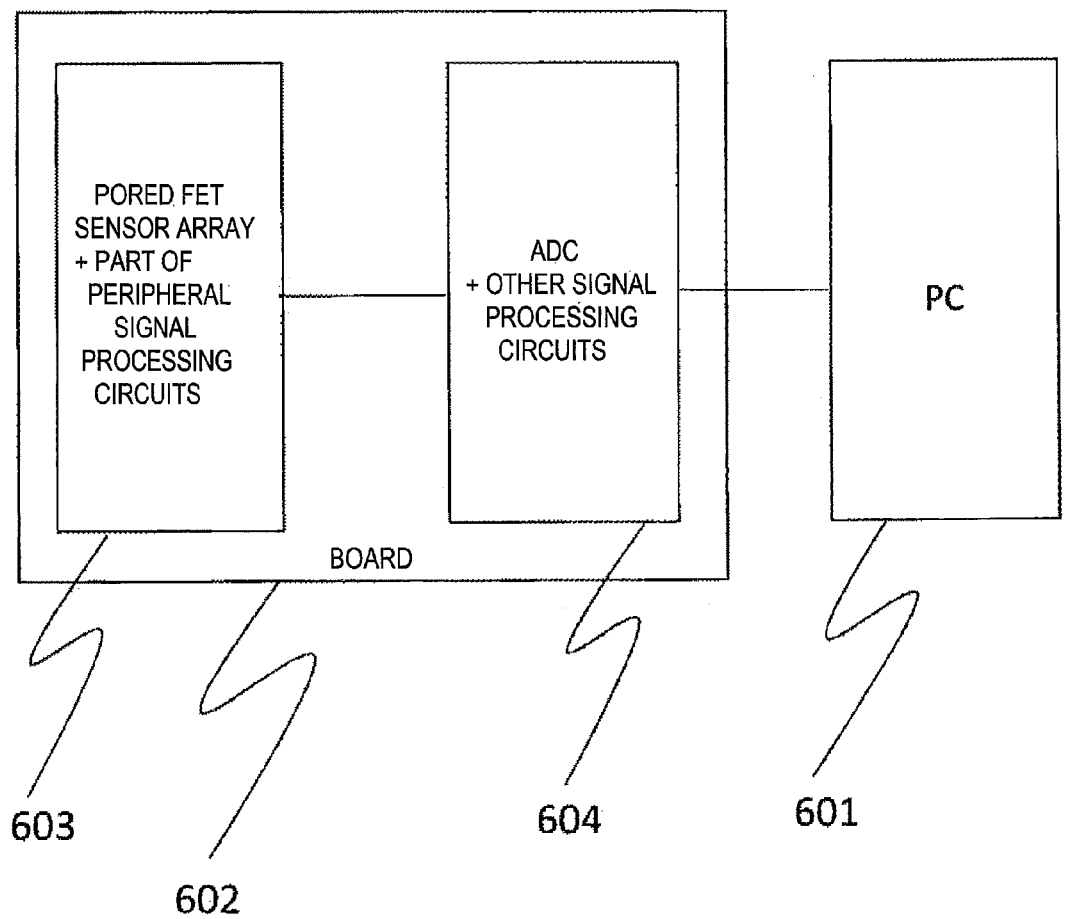

[FIG. 18]
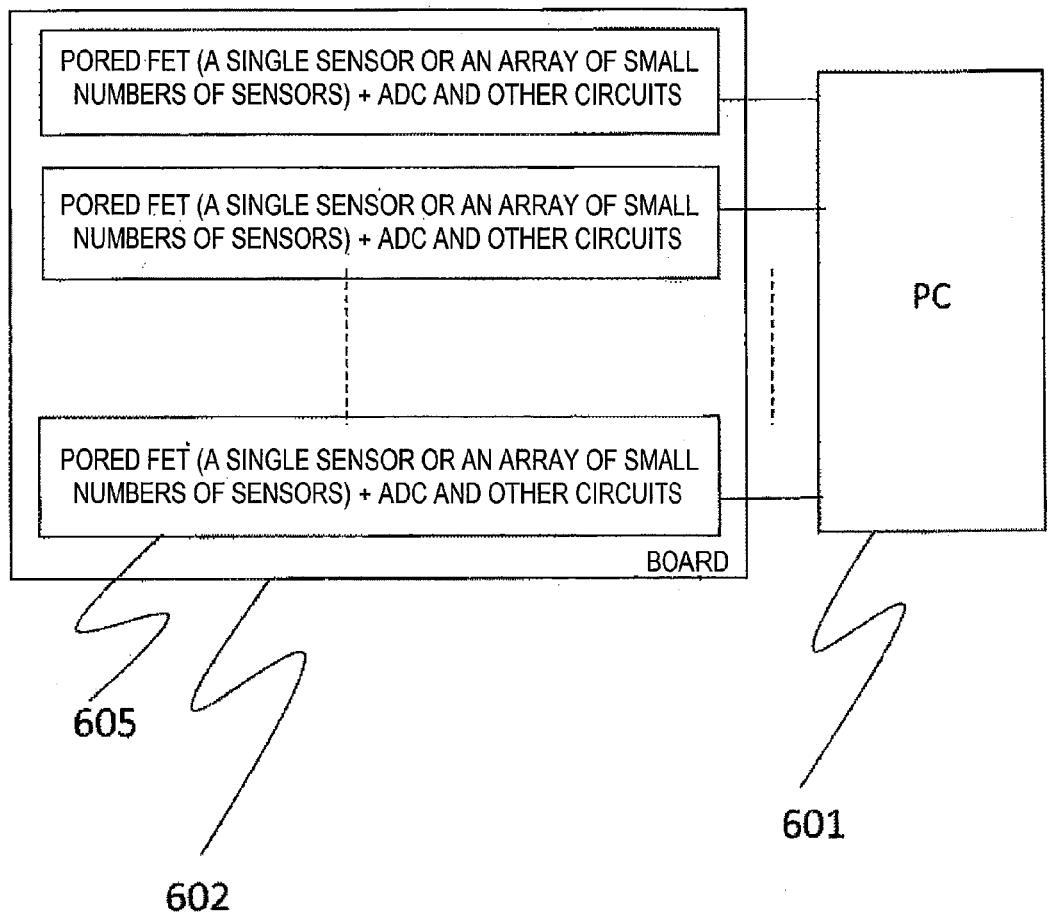

[FIG. 19]

[FIG. 20]
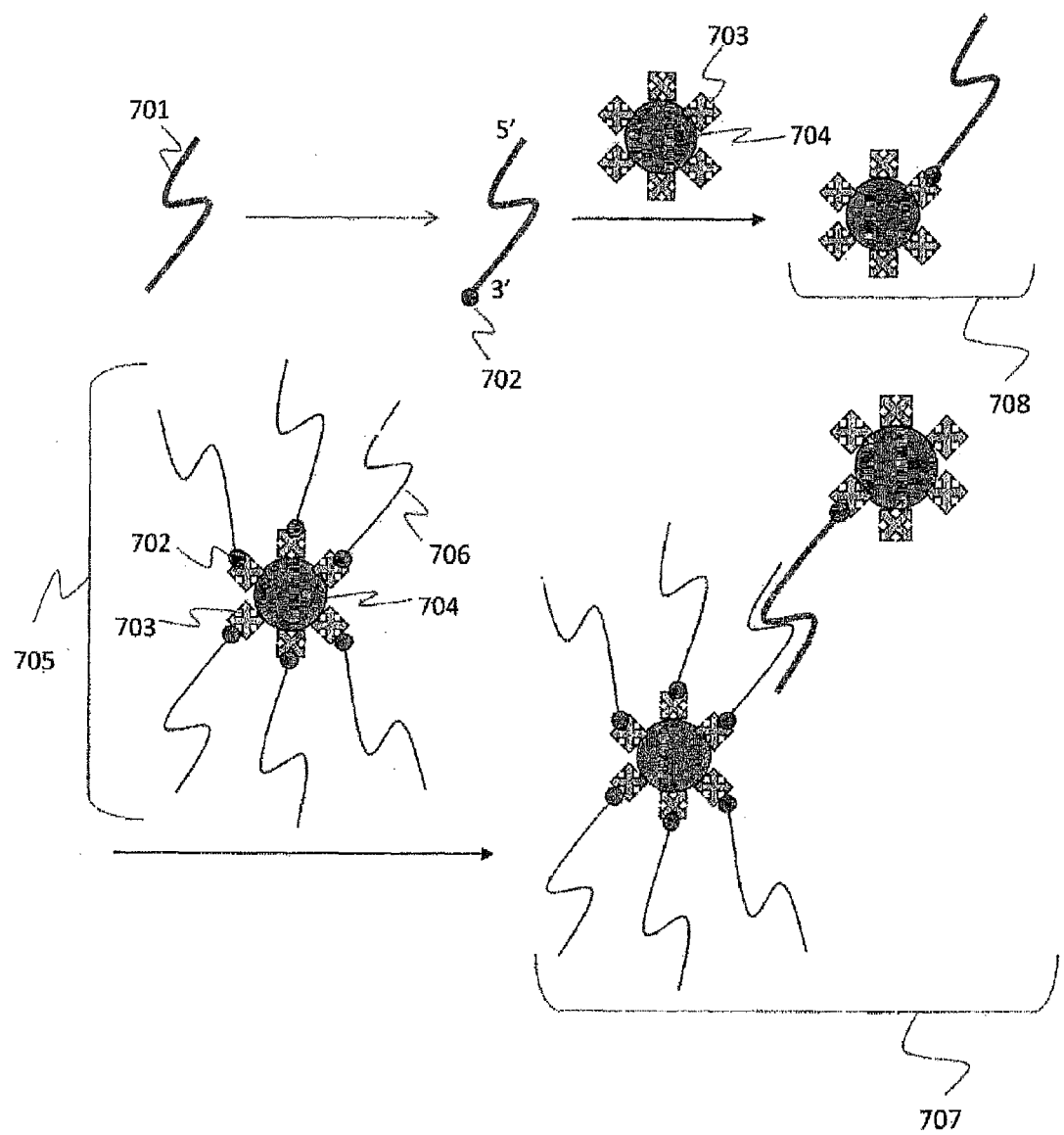

[FIG. 21]
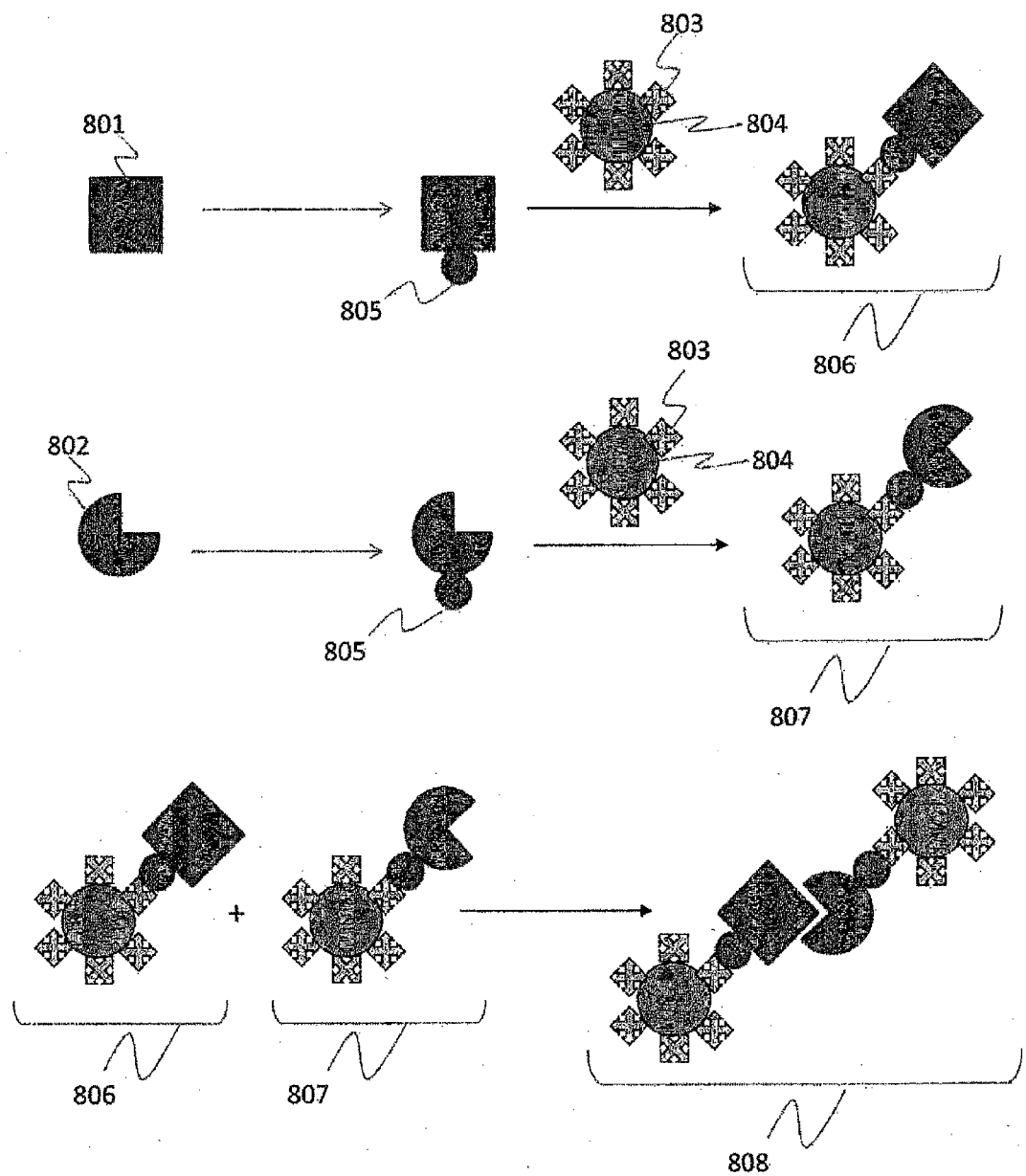

[FIG. 22]
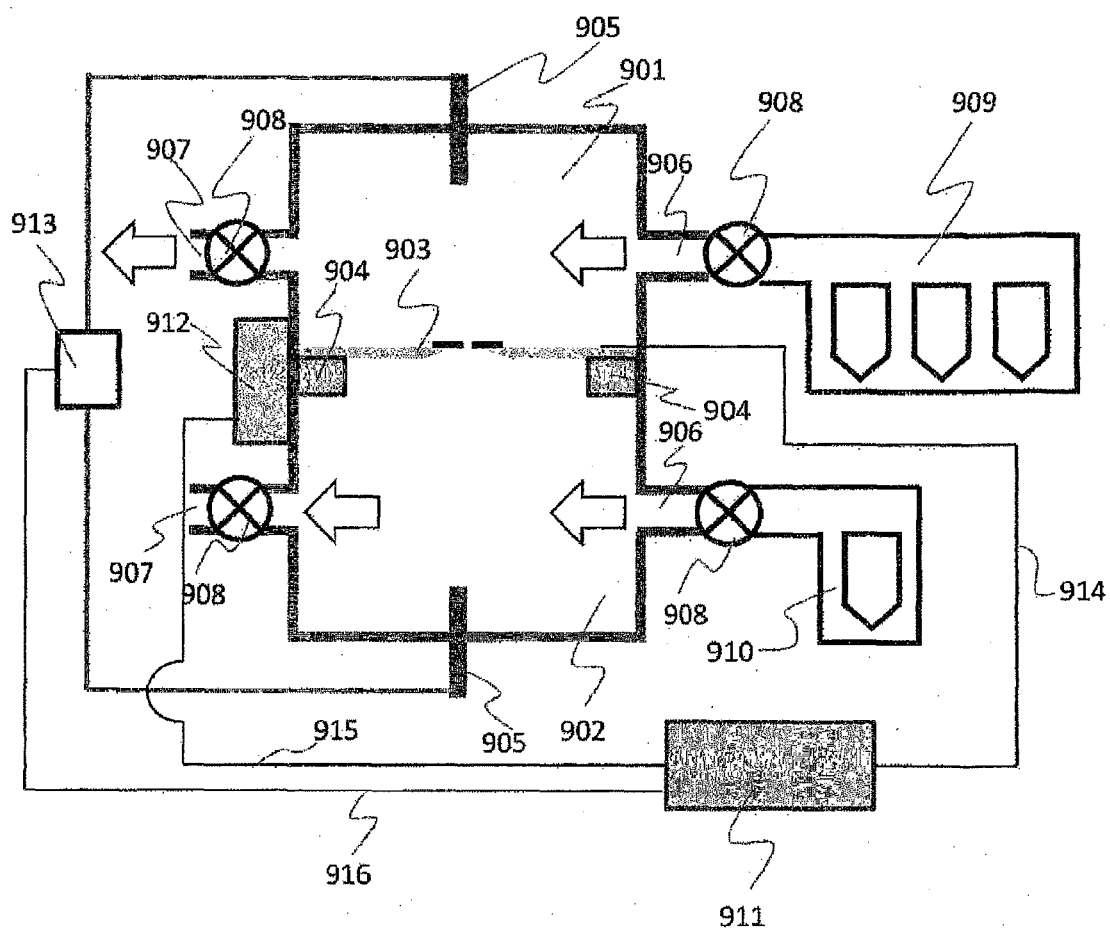

[FIG. 23]
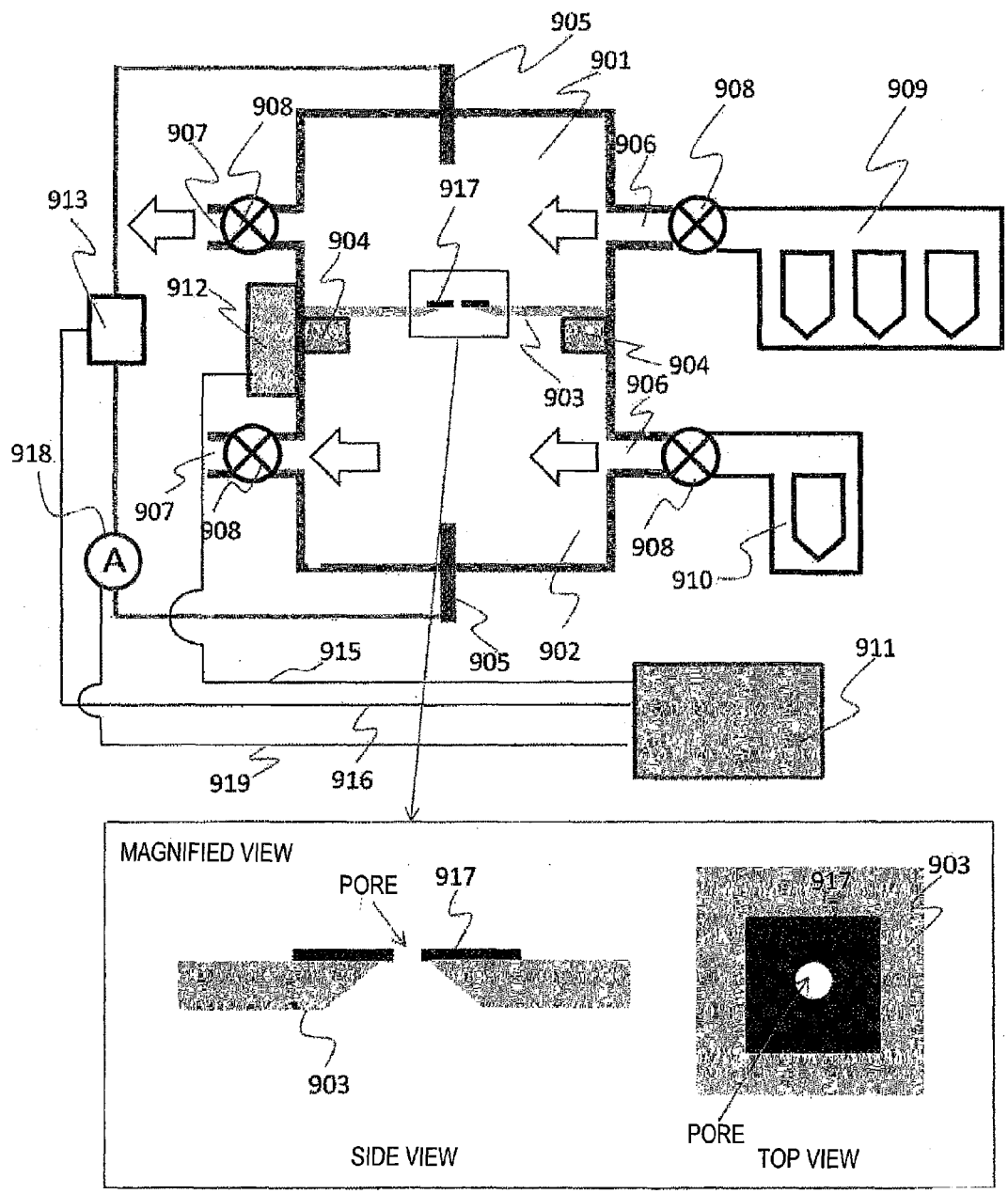

BIOMOLECULE DETECTION METHOD, BIOMOLECULE DETECTION DEVICE AND ANALYSIS DEVICE

TECHNICAL FIELD

The present invention relates to a method and a device for detecting biomolecules through current measurements.

BACKGROUND ART

Quantification of cytokines, hormones, proteins, nucleic acids, and other such biomolecules contained in bodily fluids such as a blood plasma, a lymph fluid, and a tissue fluid, or detection of trace amounts of such biomolecules contained in bodily fluids is indispensable for early diagnosis of disease and accurate identification of disease conditions.

It is thought that serum protein concentrations are on the order of $10^{-16}$ to $10^{-12}$ M in cancers (NPL 1), neurological diseases (NPL 2), and in early stages of infection (NPL 3). Among the common techniques used for quantification or detection of biomolecules are ELISA, and bead assays using chemiluminescence and flow cytometry. However, these techniques have a detection sensitivity of at most about $10^{-12}$ M (NPL 4), and are very limited in terms of its applicability to early diagnosis of disease.

For example, assume a common blood test using an about 50-µl serum sample from a subject. Here, when the marker is $10^{-17}$ M (10 aM), only about 300 molecules would be present, and a technique that counts the molecules rather than measuring the concentration would be needed. As it currently stands, no such techniques are available for practical applications, and there is a need for a detection technique with an aM-order detection sensitivity.

PTL 1 discloses a method that uses flow cytometry to determine the number of microparticles that have captured antigens.

A recently proposed digital ELISA technique enables detection of a sample containing only 10 to 20 molecules per 100 µl ($10^{-19}$ M concentration) by using antigen-antibody reaction (NPL 5). In this method, antibody-immobilized magnetic microparticles are used to capture antigens (detection target biomolecules), and are reacted with biotin-attached second antibodies, and then with streptavidin-attached galactosidase to introduce the enzyme onto the magnetic microparticles. The microparticles are then placed in an array of micro holes formed by etching the terminal of optical fiber bundles. This is acted upon by a chemiluminescence substrate, and the number of chemiluminescence spots is determined through the optical fibers to count the antigen molecules.

CITATION LIST

Patent Literature

PTL 1: Japanese Patent No. 4748542

Non Patent Literature

NPL 1: Srinivas, P. R., Kramer, B. S. & Srivastava, S. Trends in biomarker research for cancer detection. Lancet Oncol. 2, 698-704 (2001).

NPL 2: Galasko, D. Biomarkers for Alzheimer's disease—clinical needs and application. J. Alzheimers Dis. 8, 339-346 (2005).

NPL 3: Barletta, J. M., Edelman, D. C. & Constantine, N. T. Lowering the detection limits of HIV-1 viral load using real-time immuno-PCR for HIV-1 p24 antigen. Am. J. Clin. Pathol. 122, 20-27 (2004).

NPL 4: Giljohann, D. A. & Mirkin, C. A. Drivers of biodiagnostic development. Nature 462, 461-464 (2009).

NPL 5: David M Rissin et al, Nature Biotechnology, 28, 1641 (2010).

NPL 6: Fologea D. et al., Appl Phys Lett., 91, 053901-3 (2007).

NPL 7: Romero-Cano, M. S. et al., Journal of Colloid and Interface Science, 198, 266-272 (1998).

SUMMARY OF INVENTION

Technical Problem

Considering the optical system, the method disclosed in PTL 1 is not practical in terms of realizing a parallel process, and may require a long measurement time. The method disclosed in NPL 5 allows for certain levels of a parallel process. However, the number of detectable molecules in a single detection is limited by the number of optical fibers, specifically the number of micro holes in the array. This requires concentrating a sample when the concentrations is low, and, conversely, diluting a sample when the concentration is high. A problem thus remains that the detection requires adjusting the concentration in advance, and complicates the process in actual applications.

The present invention has been made in view of the foregoing problems, and it is an object of the present invention to provide a method for counting detection target biomolecules one by one, specifically a simple-procedure detection method that does not require adjusting the sample concentration in advance.

Solution to Problem

The present inventors conducted intensive studies, and developed a method for counting detection target biomolecules one by one without any limitation in the number of molecules counted.

Specifically, the method captures a biomolecule on a charge carrier immobilized with large number of detection antibodies, and the charge carrier is reacted with a different charge carrier immobilized with second antibodies to make an aggregate of charge carriers bound to each other via the biomolecule. The charge carrier aggregate is then detected in parallel with a device having substrates on which large numbers of detectors combining a field-effect transistor and a pore are provided. These large numbers of detectors can sufficiently accommodate any increase of detection target molecules.

Advantageous Effects of Invention

The present invention is intended to provide a method for detecting the target by counting the detection target biomolecules one by one in a manner not possible with conventional detection methods.

Specifically, the method uses a field-effect transistor for detection, and allows the detectors to be easily provided in parallel for easy and high-speed detection. For example, a field-effect transistor and a pore can be easily fabricated on a 1-mm$^2$ substrate in a 1-µm pitch, and, for example, 100,000 charge carrier conjugates can easily be detected per second as they pass through the pore. On average, the method enables detection of $6 \times 10^{13}$ charge carrier conjugates in 10 minutes. For example, for a 50-μl serum specimen, the same method can be used to measure a wide molar concentration range from a concentration as high as 1 μM down to a concentration as small as 1 aM (30 molecules/50 μl).

Further, because the detection is based on current changes in the field-effect transistor as they occur when the charge carriers pass through the pore, the method does not require any optical system, and can easily make the device smaller than in conventional fluorescence detections, and reduce the production cost of the device.

BRIEF DESCRIPTION OF DRAWINGS

FIG. 1 is a diagram explaining an exemplary detection method of the present invention.

FIG. 3 is a diagram explaining an exemplary configuration of the detection device of the present invention.

FIG. 4 is a conceptual diagram explaining the detection device of the present invention.

FIG. 5 is a diagram representing a method for producing the detection device of the present invention.

FIG. 6 is a diagram representing a method for producing the detection device of the present invention.

FIG. 7 is a diagram representing a method for producing the detection device of the present invention.

FIG. 8 is a diagram representing a method for producing the detection device of the present invention.

FIG. 9 is a diagram representing a method for producing the detection device of the present invention.

FIG. 10 is a diagram representing a method for producing the detection device of the present invention.

FIG. 11 is a diagram representing a method for producing the detection device of the present invention.

FIG. 12 is a diagram representing a method for producing the detection device of the present invention.

FIG. 13 is a diagram representing a method for producing the detection device of the present invention.

FIG. 14 is a diagram representing a method for producing the detection device of the present invention.

FIG. 15 is a diagram representing a method for producing the detection device of the present invention.

FIG. 16 is a diagram explaining a configuration of the detection device of the present invention.

FIG. 17 is a diagram explaining a configuration of the detection device of the present invention.

FIG. 18 is a diagram explaining a configuration of the detection device of the present invention.

FIG. 20 is a diagram explaining an exemplary detection method of the present invention.

FIG. 21 is a diagram explaining an exemplary detection method of the present invention.

FIG. 22 is a diagram explaining an exemplary configuration of the detection device of the present invention FIG. 23 is a diagram explaining an exemplary detection method and an exemplary configuration of the detection device of the present invention.

DESCRIPTION OF EMBODIMENTS

Figure 2A:
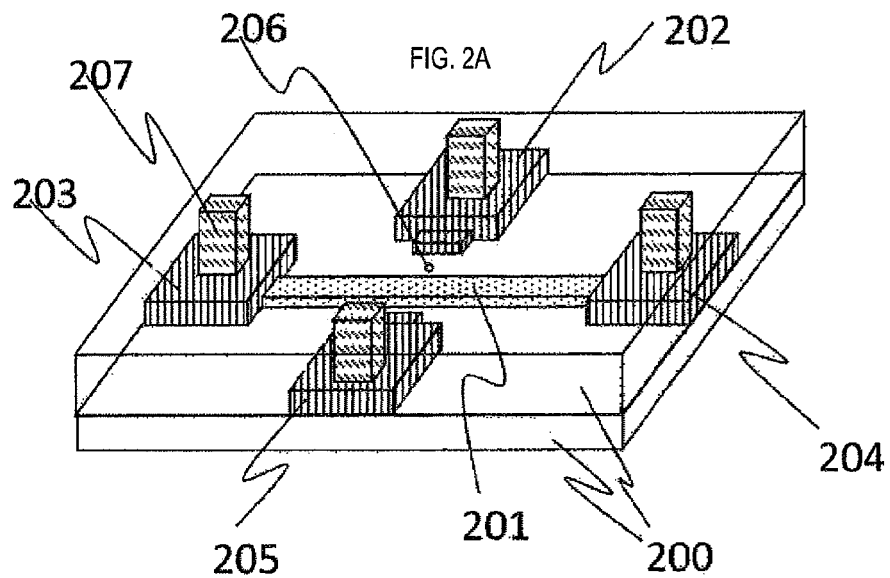
FIG. 2 is a diagram explaining exemplary configurations of a detection device of the present invention.

Disclosed in an embodiment of the present invention is a biomolecule detection method that includes reacting a detection target biomolecule with a charge carrier having a surface with a first antibody against the biomolecule, and a charge carrier having a surface with a second antibody against the biomolecule; measuring an amount of charge of each of the charge carriers to detect a conjugate of the charge carriers; and evaluating the abundance the biomolecule. As used herein, evaluating the abundance of biomolecules means counting the molecules. This is indeed the same as measuring a concentration when the subject of measurement is a liquid and when the total volume or amount is known.

Disclosed in another embodiment is a biomolecule detection method that includes: passing a reaction liquid through a pore that penetrates through a substrate from one surface to the other surface of the substrate, the reaction liquid being obtained by reacting a detection target biomolecule, a charge carrier having a surface with a first antibody against the biomolecule, and a charge carrier having a surface with a second antibody against the biomolecule, the substrate having a surface with opposing two electrodes, and the pore penetrating through the substrate between the electrodes; measuring the current between the electrodes to detect a conjugate of the charge carriers; and evaluating the abundance of the biomolecule.

Disclosed in another embodiment is a biomolecule detection method that uses a substrate with a surface provided with an insulating film, a control gate, a source, a drain, a channel, and a pore that penetrates through the substrate from one side to the other side of the substrate from a flat surface on which the control gate, the source, the drain, and the channel are mounted, the substrate being a field-effect transistor that with the control gate exhibits an electric field effect on the channel, and the pore being disposed between the side surface of the control gate facing the channel and the vicinity of the side surface of the channel facing the control gate. The method passes the reaction liquid through the pore, detects a conjugate of the charge carriers from a change in the current passing from the source to the drain, and evaluates the abundance of the biomolecule.

Disclosed in another embodiment is a biomolecule detection method in which the charge carriers are one selected from magnetic microparticles, polymer microparticles, proteins, and nucleic acids.

Disclosed in another embodiment is a biomolecule detection device that includes: means that causes a reaction between a detection target biomolecule, a charge carrier having a surface with a first antibody against the biomolecule, and a charge carrier having a surface with a second antibody against the biomolecule; and means that measures an amount of charge on each individual charge carrier.

Disclosed in another embodiment is a biomolecule detection device in which the means that measures an amount of charge on each individual charge carrier is a device provided with a field-effect transistor and a through pore.

Disclosed in another embodiment is a biomolecule detection method that uses a device having a first solution tank, a second solution tank, a film, and electrodes, the film separating the first solution tank and the second solution tank from each other and having a through pore, the electrodes being provided on the first solution tank and the second solution tank to measure a current that generates as a result of movement of a substance through the through pore. The method uses a reaction liquid obtained through a reaction between a detection target biomolecule, a charge carrier having a surface with a first antibody against the biomolecule, and a charge carrier having a surface with a second antibody against the biomolecule, and charges the reaction liquid into the first solution tank, detects a change in the current passing between the first solution tank and the second solution tank to detect a conjugate of the charge carriers, and evaluates the abundance of the biomolecule.

In the biomolecule detection method of an embodiment of the invention, the through pore has a diameter that is larger than the diameters of the charge carriers used, and that is smaller than two times the diameters of the charge carriers. The film thickness is desirably no greater than two times the diameters of the charge carriers.

Disclosed in another embodiment is that the charge carriers used in the biomolecule detection method are selected from magnetic microparticles, polymer microparticles, proteins, and nucleic acids.

Disclosed in another embodiment is a biomolecule detection device that includes: an apparatus that includes a first solution tank, a second solution tank, a film, and electrodes, the film separating the first solution tank and the second solution tank from each other and having a through pore, the electrodes being provided between the first solution tank and the second solution tank to measure a current that generates as a result of movement of a substance through the through pore; means that causes a reaction between a detection target biomolecule, a charge carrier having a surface with a first antibody against the biomolecule, and a charge carrier having a surface with a second antibody against the biomolecule; and means that charges a reaction liquid into the first solution tank, and detects a change in a current passing between the first solution tank and the second solution tank.

In the appended figures provided to describe certain embodiments of the present invention, functionally the same components are given the same reference numerals, and are not described repeatedly to avoid redundancy to the best extent possible. Embodiments of the present invention are now described in detail with reference to the accompanying drawings. The device structures and the materials described in the embodiments serve to solely illustrate implementations of the spirit of the present invention, and are not intended to strictly specify materials, dimensions, and other such variables in any ways.

Embodiment 1

The concept of the present invention is described below with reference to the schematic diagram of FIG. 1.

FIG. 1 shows a sandwich conjugate 105 that results from the reaction of a first antibody 102 and a second antibody 104 that specifically bind to a detection target biomolecule 101. A functional group 103 is attached to the first antibody 102 and the second antibody 104 in advance. In order to efficiently obtain the sandwich conjugate 105, it is preferable to use a reaction method in which a monoclonal antibody and a polyclonal antibody are used as the first antibody 102 and the second antibody 104, respectively, and in which these are reacted one after another.

FIG. 1 also shows a dimer 109 that results from the sandwich conjugate 105 and a charge carrier 107. For the binding of the charge carrier 107 and the sandwich conjugate 105, a binding molecule 108 that specifically binds to the functional group 103 is attached to the charge carrier 107 in advance. For example, a biotin and a streptavidin may be used for the functional group 103 and the binding molecule 108, respectively.

The dimer 109 of the charge carriers 107 sandwiching the biomolecule 101 can be obtained by reacting the sandwich conjugate 105 with the charge carrier 107 decorated with the binding molecule 108 on the surface.

In order to efficiently obtain the sandwich conjugate 105, it is preferable to react the first antibody 102 and the second antibody 104 in concentrations that are 10 times, more preferably at least 100 times greater than the concentration of the biomolecule 101.

For the reaction of the charge carrier 107 with the sandwich conjugate 105, it is preferable to react the charge carrier 107 in concentrations that are at least 10 times, more preferably at least 100 times greater than the concentration of the sandwich conjugate 105 so that the number of attached sandwich conjugates 105 per charge carrier 107 can be sufficiently reduced. The dimer 109 of the charge carriers 107 sandwiching the biomolecule 101 is then measured with a detection device 114 for the number of biomolecules 101.

The detection device 114 is disposed on a support 113 in numbers as may be decided according to the detection throughput. The support 113 is disposed to separate a first solution tank 111 and a second solution tank 112. The detection devices 114 are each provided with a source 116, a drain 117, a control gate 115, and a channel 121 formed on a substrate 119. A pore 118 is a hole that penetrates through the substrate 119, and is provided between the control gate 115 and the channel 121 in a region on the substrate 119, or in a region including the channel 121 either in part or as a whole.

A reaction liquid containing the dimer 109 of the charge carriers 107 sandwiching the biomolecule 101, and a reaction product 110 other than the dimer is charged into the first solution tank 111, and, for example, an electric field is applied across the first solution tank 111 and the second solution tank 112 to move the reaction product containing the charge carriers 107 from the first solution tank 111 to the second solution tank 112 through the pore 118. The detection device 114 is a field-effect transistor that exerts an electric field effect on the channel 121 with the control gate 115. The pore 118 is provided in the vicinity of the channel 121, and the passage of the charge carriers 107 through the pore 118 is detected by measuring changes in the current passing from the source 116 to the drain 117 as they occur when the charge carriers 107 pass through the pore 118.

The device identifies whether the passage of the charge carriers 107 occurs in the form of a monomer or the dimer 109 of the charge carriers 107 sandwiching the biomolecule 101, and counts the dimers 109 to evaluate the abundance of the biomolecules 101. Unreactants 106, the reaction product 110 other than the dimer, and the dimer 109 can be sufficiently discriminated against each other by measuring the amounts of current changes.

The charge carriers 107 may use microparticles of polymers such as polystyrene. The amount of surface negative charge can be controlled by controlling the density of the carboxyl group introduced to the surfaces of the charge carriers 107. Alternatively, the charge carriers 107 may have a positive charge imparted by an amino group introduced to the surface of polymer microparticles, and the amount of positive charge can be controlled by controlling the density of the amino group.

The charge carriers 107 may use proteins. For example, the charge carriers 107 may be used as negatively charged charge carriers when BSA (bovine serum albumin) is used. When using polymer microparticles, it is required to sufficiently reduce aggregation, or sufficiently remove aggregates before use. This is because any such aggregates may cause problems in distinguishing between aggregates and the dimer 109 of the charge carriers 107 sandwiching the biomolecule 101. On the other hand, the advantage of using proteins as the charge carriers 107 is that proteins do not involve the aggregate issue. Preferred for use as proteins are spherical proteins for advantages such as solubility in water.

The charge may be positive or negative, and should preferably be as large as possible. From this standpoint, it is preferable to use microparticles of polymers such as polystyrene.

Identification of the dimer may become difficult when the individual monomeric charge carriers 107 enter the pores in series. Such error can be prevented by increasing the amount of the charge on the charge carriers 107 and creating an electrostatic repulsion that prevents the charge carriers 107 from having the same distance as the dimers.

The diameter of the charge carriers 107 needs to be smaller than the diameter of the pores 118. More preferably, the charge carriers 107 should preferably have small diameters, specifically 10 μm or less, more preferably 2 μm or less from the standpoint of dispersibility and diffusion rate in liquid.

The diameter of the pore 118 needs to be larger than the diameter of the charge carriers 107. Preferably, the pore 118 is at most twice as large as the diameter of the charge carriers 107 to meet the need for distinguishing between the unreacted monomers and the biomolecule-conjugated dimers 109.

The current through the channel 121 varies with the electric field changes caused by the effective charge amount or the effective electric field of the charge carriers 107 passing through the pore 118, and the charge carriers 107 are identified as monomers or dimers by detecting such changes. The current layer through the channel 121 needs to be made as thin as possible for the detection of the current originating in the electric field changes caused by a single charge carrier 107. To this end, the thickness of the channel 121 needs to be reduced. The charge carriers 107 passing through the pore 108 can be detected one by one, and the dimer 119 and the reaction product 110 other than the dimer 119 can be discriminated against each other by making the thickness of the channel 121 thinner than the diameter of the charge carriers 107.

FIG. 2 is a diagram showing detailed configurations of the detection device 114.

The detection device 114 includes an insulating film 200, a channel 201, a control gate 202, a source 203, a drain 204, a backgate 205, a pore 206, and wires 207 providing contacts for the members 202 to 205.

Figure 2B:
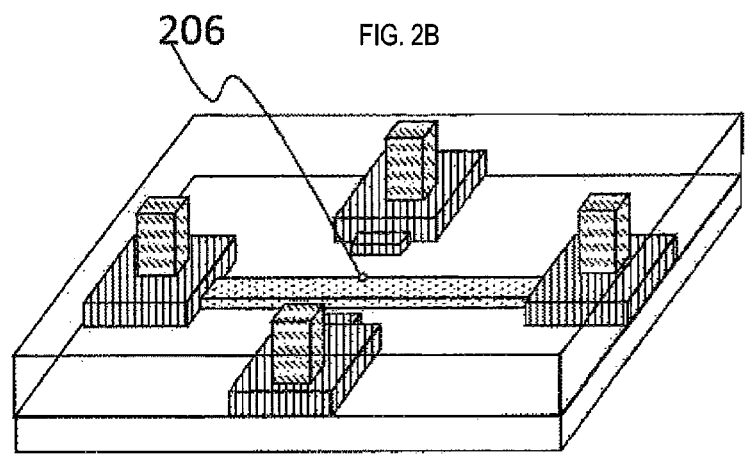
Figure 2C:
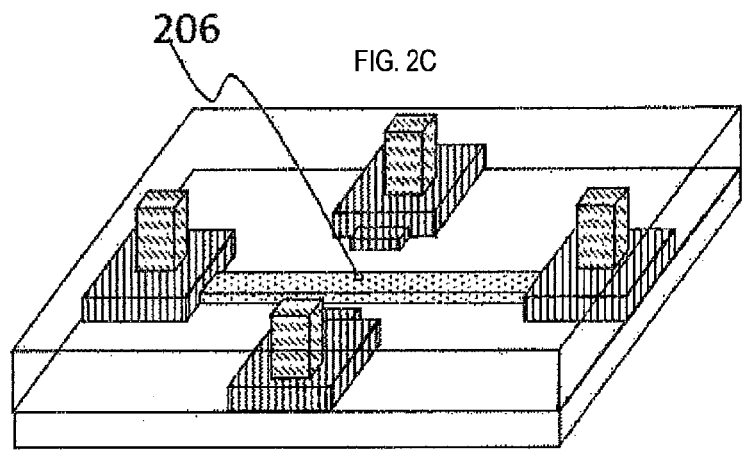

The pore is provided between the side surface of the control gate facing the channel and the side surface of the channel facing the control gate (FIG. 2A). Alternatively, the pore may be provided at an edge of the channel facing the control gate (FIG. 2B), or inside the channel in the vicinity of the side surface of the channel facing the control gate (FIG. 2C).

For example, the channel 201 is a non-doped silicon, a P-type silicon, or a low-concentration N-type silicon. The control gate 202 and the backgate 205 are N-type or P-type silicons. The source 203 and the drain 204 are N-type silicons.

The device is what is known as a side-gate transistor, operating under the controlled gate voltage with an applied source-drain voltage (source voltage<drain voltage). While the transistor is ON, an inversion layer is induced at the channel side portion on the side of the control gate (pore side), and the current passes along the channel side portion on the control gate side. The inversion layer has a very thin thickness, about 1 to 3 nm or less, though the thickness varies with the control gate voltage.

With the inversion layer effect and the thicknesswise quantum well trapping effect of the foregoing configuration, a pseudo one-dimensional narrowest current path can be formed in the side wall portion of the thin film channel. With the pseudo one-dimensional narrowest current path, the device is very sensitive to the minute electric field changes due to the subject in the pore. This makes it possible to greatly increase the rate of detection signal change (detection sensitivity).

The channel current is due to the electrons induced by the electric field of the control gate. It is therefore desirable to dispose the pore between the control gate and the channel current path. In this way, a potential change due to the subject in the pore can very effectively modulate the electric field between the control gate and the channel, and reflect the change in the channel current.

Detection sensitivity improves as the pore comes closer to the current path in the side portion of the channel. In the extreme case, for example, as shown in FIGS. 2B and 2C, the pore is a part of the channel side portion, or the pore is very close to the channel side portion. On the other hand, for example, the current change due to the subject in the pore is very small when the pore is disposed between the current path of the channel side portion on the control gate side and the backgate. This is because the electric field created by the control gate in the channel can be hardly modulated when the pore is disposed on the backgate side.

FIG. 3 shows a region 300 desirable for pore formation. Desirably, the pore is disposed between the control gate and the channel side portion, within the pseudo one-dimensional narrowest current path of the channel side portion.

Very high sensitive sensing is possible when the pore region is a part of the channel as in FIGS. 2B and 2C. On the other hand, when the channel and the pore are separated from each other with the insulating film as in FIG. 2A, the channel does not directly contact the subject or the solution containing the subject, and problems such as channel corrosion and changes in the state of the channel surface become less likely to occur. This improves device reliability.

The spread of the current path along the channel width direction can be effectively prevented, and a stable one dimensional electron conduction path can be effectively formed in the channel side portion by applying a voltage to the backgate 205, and controlling the electric field in such a manner that electrons concentrate more on the control gate side.

FIG. 4 shows a model representing a pore and two flanking capacitors from the region of the device indicated by broken lines.

C1 represents a capacitor between the control gate and the pore in the region inside the broken lines, and C2 represents a capacitor between the pore and the channel in the region inside the broken lines. It is assumed here that the device has, for example, a pore size of 20 nm, a distance of 50 nm between the control gate and the pore, a thickness of 3 nm between the channel and the control gate, and uses an oxide film (relative permittivity 3.9) as the insulating film between the control gate and the pore. In this case, C1 is about $2.76 \times 10^{-19}$ F when the pore is approximated by a quadrangular prism measuring 20 nm on one side.

When a change in charge amount in the pore is $\Delta Q$, the threshold voltage shift $\Delta Vth$ at the channel edge in the vicinity of the pore is represented by the following equation (1).

$$\Delta Vth = \Delta Q/C1 \qquad \text{Equation (1)}$$

Assume here that a spherical protein BSA (bovine serum albumin, diameter: 7 to 8 nm) is used as the charge carrier. Knowing that the amount of surface charge on BSA at pH 7 is −18 e from NPL 6, the threshold shift difference when passing a single molecule of BSA and two molecules of BSA through a pore (diameter 20 nm) becomes very large at $\Delta Vth=10.4$ V.

In the case of using a polystyrene bead having a diameter of about 40 nm as the charge carrier, for example, the amount of surface charge on the bead can be estimated to be about $1.6\times10^{-16}$ C from the surface charge density ($-3.2$ $\mu C/cm^2$) of polystyrene when potassium per sulfate is used as the initiator as described in NPL 7. With a device configuration with a pore size of 80 nm, the threshold shift difference when passing a single polystyrene bead and two polystyrene beads becomes very large at $\Delta Vth=36.2$ V.

The present device can achieve a threshold voltage shift close to such ideal values. This is for the following reasons. First, because of the very narrow one dimensional electron conduction formed as the current path at the edge of the thin film channel, the electric field change (threshold change) at the edge of the channel in the vicinity of the pore is essentially reflected in the threshold change of the transistor. (A large threshold shift is not obtained when the channel is thick and the current path is wide in thickness direction because the current passes a region distant away from any incoming single charge. The same is the case when the current passes over the whole surface in the width direction of the channel, and it is not possible to obtain a large threshold shift. A large threshold shift close to such large values can only be achieved with the configuration and the operating mode of the present device.)

An electric field between the control gate and the channel that moves around the side of the pore into the channel can be blocked by bringing the pore and the channel close to each other, or by contacting the pore and the channel. This ensures that the electric field modulation in the pore is fully conducted to in the channel, and a large threshold shift such as above can be achieved.

As described above, with proteins or polymer microparticles used as the charge carriers, the detection device of the present invention can detect a large potential difference between the carrier passed as a monomer and the carrier passed as a dimer, making it possible to detect and identify these carriers with sufficient detection sensitivity.

In a detection performed under a constant control gate voltage, current changes due to the charge carriers passing through the pore can be adjusted by adjusting the distance between the pore and the channel, or the distance between the pore and the control gate. A current change due to charge carriers increases as the distance between the pore and the control gate is increased. From equation (1), a current change due to charge carriers also increases as the dielectric constant between the pore and the control gate becomes smaller. A current change also can be increased by adjusting the amount of the effective charge of the charge carrier through pH adjustment. Such improvement of detection sensitivity is another notable advantage of the present device. This is by virtue of the pore being disposed between the channel current path and the control gate. The distance between the pore and the control gate is set to a distance that provides the highest detection sensitivity, taking into account factors such as usable voltages and voltage resistance in a comprehensive manner.

The backgate is not necessarily required in the present device. The effects of the backgate include concentrating the current path more toward the pore side, and adjusting the threshold voltage.

Embodiment 2

An example of the production process of the detection device used in the present invention is described below with reference to FIGS. 5 to 14.

The producing method of the present invention is not limited to the following processes. In each figure, the process flow is represented by (a), (b), and (c), in which (c) is a top view, (a) is a cross sectional view at A-A' of (c), and (b) is a cross sectional view at B-B' of (c).

Process 1

A SiN film 209 and a $SiO_2$ film 210 are deposited on a Si substrate 208. For example, the SiN film and the $SiO_2$ film are each deposited in a thickness of 15 nm (FIG. 5).

Process 2

An N-type polysilicon 211 is deposited, and patterned into a control gate, a backgate, a source, and a drain region. For example, the N-type polysilicon is deposited in a thickness of 100 nm (FIG. 6).

Process 3

A non-doped thin film polysilicon layer 212 is formed. This thin film may be formed, for example, by depositing amorphous silicon and annealing and crystallizing it, or by depositing and oxidizing amorphous silicon or polysilicon. A thin film silicon channel with a thickness of 5 nm or less can be formed by using these methods (FIG. 7).

Process 4

A $SiO_2$ film 210 is deposited in a thickness of, for example, in 10 nm (FIG. 8).

Process 5

The $SiO_2$ film and the non-doped polysilicon are patterned into a channel by dry etching. The non-doped silicon layer covering the gate, the source, and the drain region are processed as shown in FIG. 9 (FIG. 9)

Process 6:

A $SiO_2$ film 210, a SiN film 209, a $SiO_2$ film 210, and a SiN film 209 are deposited in order as interlayer films. For example, the thicknesses are $SiO_2$/SiN/$SiO_2$/SiN=20 nm/10 nm/150 nm/200 nm from the bottom (FIG. 10).

Process 7

Contacts for the control gate, the backgate, the source, and the drain are formed. For example, Al is used as the material of the wires 207 (FIG. 11).

Process 8

The SiN film 209 is formed as an interlayer film on the wires, and a pad 215 for contacting the wires is formed. The deposition thickness is, for example, 200 nm (FIG. 12).

Process 9

The film is dry etched above and near (213) the channel (FIG. 13)

Process 10:

The Si wafer back surface is anisotropically etched with a KOH or TMAH liquid to form a thin film region. The etching mask is desirably a SiN film, for example (FIG. 14).

Process 11

A pore 214 is then formed in the regions described above (the region between the control gate and the channel side portion, and the region at the channel side portion where a pseudo one-dimensional narrowest current path is formed).

A micro pore measuring 50 nm or less can be formed by, for example, boring with a TEM beam. Dry etching may be performed to form a pore of any diameter between 50 to 1000 nm (FIG. 15). The desirable pore diameter depends on the size of the charge carrier used for analysis, and needs to be larger than the diameter of the charge carrier so as to allow for passage of the charge carrier. Desirably, the pore diameter is smaller than two times the diameters of the charge carrier because measurement errors may occur when two or more charge carriers pass through the pore at once.

Referring to FIG. 15(c), the device includes a source 215A, a drain 215B, and a channel 215E. The source 215A and the drain 215B may be reversed, and electrons flow through the channel 215E in a direction from the source 215A to the drain 215B. The device also includes a gate 215C and a backgate 215D. The backgate 215D may be omitted. The pore 214 is formed between the channel 215E and the gate 215C.

The device can be formed in the manner described in these processes. The foregoing processes describe an example in which the channel is formed by using polysilicon. However, the transistor may be formed with an SOI wafer by repeatedly oxidizing and washing the SOI and forming a thin film in a region corresponding to the channel region. Though this requires accurate thickness management, the monocrystalline Si channel can produce stable and high current values in detections. The stable detection signal can improve the accuracy of identification, and the increased detection current value makes processing of detection signals easier and faster.

Embodiment 3

Referring to FIGS. 16 to 19, the following describes examples of the device of the present invention, along with examples of systems that display the abundance of the target molecule from detection signals obtained from the device.

Referring to the system block diagram of FIG. 16, a pored FET sensor (a single sensor or an array of sensors) of the present invention, and signal processing circuits such as an ADC unit for converting signals detected by the sensor are provided on a chip 600 of a semiconductor substrate. Output signals are sent to a PC 601, and the PC displays the number of detected dimer charge carriers, specifically the number of detection target molecules.

When provided as an array, the sensors can analyze the detection target molecules in parallel. This increases the number of detection signals, and improves the reliability of the analysis result. Because the sensor array, ADC, and other peripheral signal processing circuits are formed on a single chip, it is possible to reduce the module size, and the overall size of the system. The integration also can help lower manufacturing cost.

Referring to the system block diagram of FIG. 17, a chip 603 with a pored sensor (a single sensor or an array of sensors) and a part of peripheral circuits is coupled on a board 602 to a chip 604 provided with an ADC and other signal processing circuits. Output signals are sent to a PC, and the PC displays the number of detected dimer charge carriers, specifically the number of detection target molecules.

The chip that primarily serves as a sensor portion should be provided as a replaceable chip by being separately provided from the chip of primarily signal processing circuits when the pored FET sensor portion needs to be frequently replaced for improved measurement accuracy. In this way, the analysis cost can be reduced.

Referring to the system block diagram of FIG. 18, chips 605 provided with a pored FET sensor (a single sensor or an array of small numbers of sensors), ADC, and other signal processing circuits are disposed in parallel on a board 602. Output signals are sent to a PC, and the PC displays the number of detected dimer charge carriers, specifically the number of detection target molecules.

Forming the pored FET sensor (a single sensor or an array of sensors), ADC, and other signal processing circuits on a single chip reduces the production load, simplifies the chip production, and improves the yield as compared to integrating a large-scale pored FET array, ADC, and peripheral signal processing circuits on a single chip. Further, the analysis cost can be reduced because the number of parallel sensors can be decided as desired for analyses.

Figure 19A:
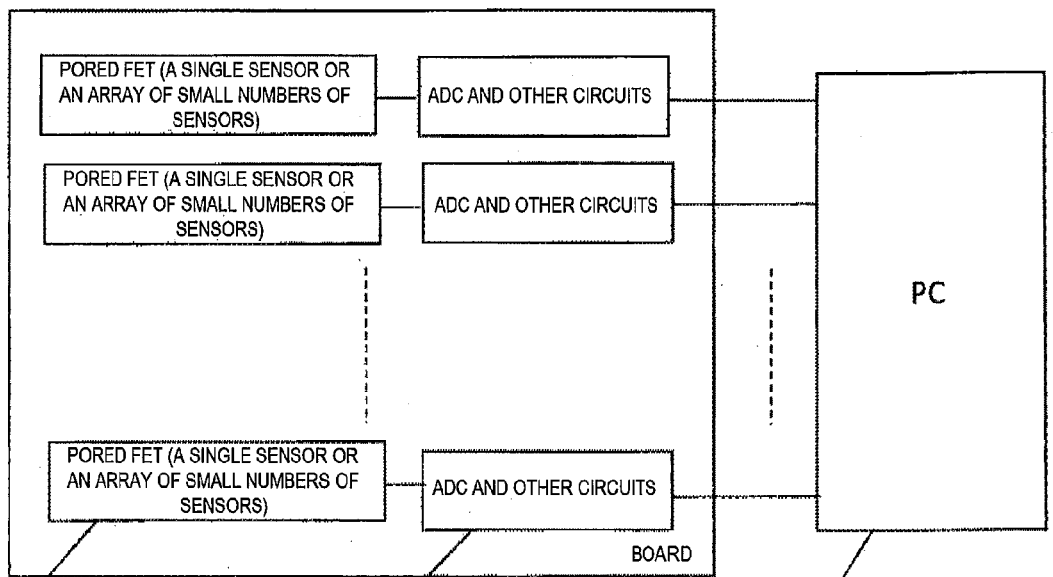
FIG. 19 is a diagram explaining configurations of the detection device of the present invention.
Figure 19B:
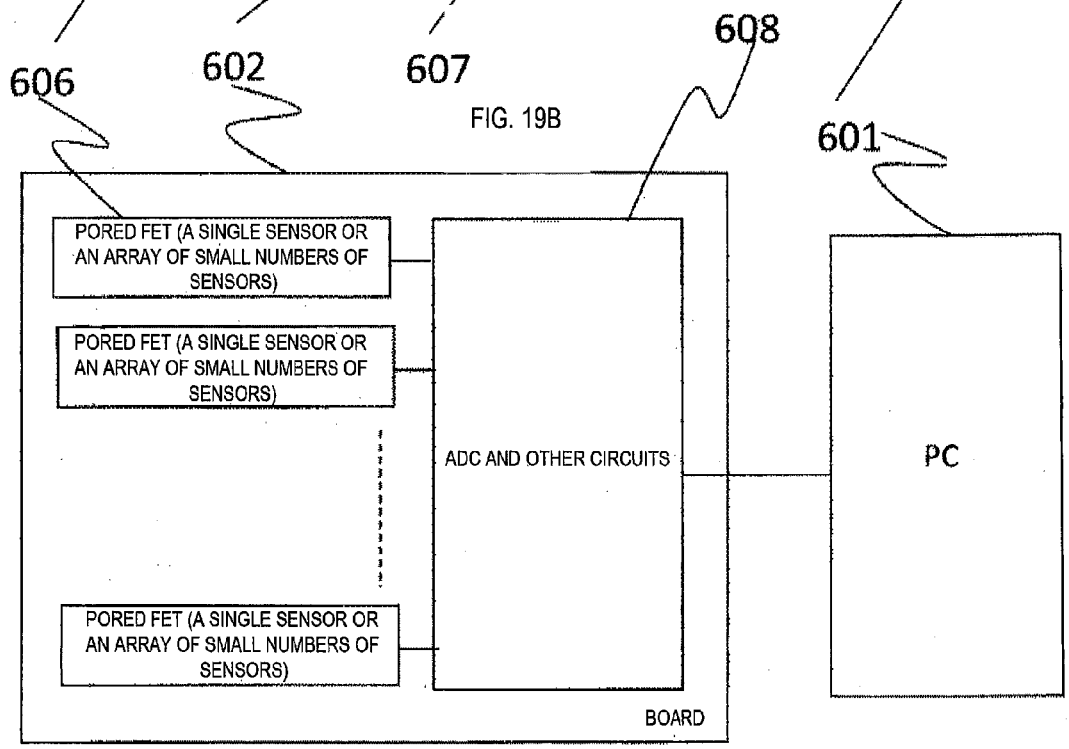

Referring to the system block diagrams of FIGS. 19A and 19B, chips 606 of primarily a pored FET sensor (a single sensor or an array of small numbers of sensors) are separately provided from ADC and peripheral signal processing circuit portions 607 and 608, and these are coupled to each other on a board.

Because the pored FET sensor (a single sensor or an array of small numbers of sensors) is separately formed from the ADC and peripheral signal processing circuits, it is possible to reduce the production load, making it easier to produce individual chips, and improving the yield. This configuration also allows for replacement of only the chips serving as the pored FET sensor. Because the sensor portion is replaceable, only the deteriorated sensor portion can be replaced. This contributes to further reducing the analysis cost.

Embodiment 4

A detection method of the present invention using a nucleic acid as the detection target biomolecule is described below with reference to the schematic diagram of FIG. 20.

A charge carrier 704 is attached to a detection target nucleic acid molecule 701. As an example, an end of the nucleic acid molecule 701 is decorated, and a second functional group 703 that specifically binds to a first functional group 702 introduced to the end of the nucleic acid molecule 701 is attached to the charge carrier 704 in advance. For example, a biotin may be used as the first functional group 702, and an avidin or streptavidin may be used as the second functional group 703. The biotin may be attached to an end of the nucleic acid molecule, for example, by attaching a biotinylated oligo to the end with an enzyme such as a terminal deoxynucleotidyl transferase. In the case of using an avidin or a streptavidin as the second functional group 703, commercially available polystyrene beads surface-coated with avidin or streptavidin may be used, for example, when polystyrene beads are used as the charge carriers 704. For example, commercially available products such as FluoroSpheres (Invitrogen) may be used.

By reacting the nucleic acid molecules 701 after the addition of the first functional group 702 with the charge carriers 704 (with the second functional group 703 attached on the surface) used in amounts 10 times, more preferably 100 times the amount of the nucleic acid molecule 701, no more than one nucleic acid molecule 701 will be immobilized on a single charge carrier 704, and 90% or more of the charge carriers 704 with the immobilized nucleic acid molecules 701 will have only a single nucleic acid molecule 701 (708 in FIG. 20), as can be easily predicted by Poisson probability.

A charge carrier 704 attached via the first functional group 702 and the second functional group 703 to a nucleic acid probe molecule 706 having a base sequence complementary to the detection target nucleic acid molecule 701 is produced in advance. A combination of biotin and avidin or streptavidin can easily be used for the first functional group 702 and the second functional group 703, as above.

A dimer 707 can be obtained by hybridizing a charge carrier conjugate 705 produced in advance as above with the charge carrier 708 that has had only a single nucleic acid molecule 701 immobilized thereon.

The charge carrier conjugate 705 is not necessarily required to immobilize only a single nucleic acid probe molecule 706, and it is rather more preferable in terms of hybridization efficiency that more than one nucleic acid probe molecule 706 is immobilized on the charge carrier 704. In order to efficiently obtain the dimer 707, the charge carrier conjugate 705 is preferably used in excess amounts, preferably in amounts about 10 times greater than the amount of the charge carrier 708 that has had only a single nucleic acid molecule 701 immobilized thereon.

The dimer 707 can be detected with high sensitivity with the method and the detection device of Embodiment 1 in the manner described therein. Specifically, the unreacted monomer, and the dimer 707 reflecting the abundance of the detection target nucleic acid molecule 701 can be clearly identified and detected by measuring the amount of current change based on the amount of charge passing through the pore.

Embodiment 5

A detection method of the present invention that examines the presence or absence of protein interactions is described below with reference to the schematic diagram of FIG. 21.

Charge carriers 804 are separately attached to a first protein 801 and a second protein 802. To this end, a first functional group 805 is attached to proteins 801 and 802, and a second functional group 803 that specifically binds to the first functional group 805 is attached to the charge carriers 804.

For example, a biotin may be used as the first functional group 805, and a biotin may desirably be expressed with the C or N terminal when producing proteins in an acellular expression system. For example, it is possible to easily introduce biotin by using a commercially available reagent (RTS AviTag *E. coli* biotinylation kit; Roche Diagnostic).

An avidin or a streptavidin may be used as the second functional group 803. For example, when using polystyrene beads as the charge carriers 804, commercially available polystyrene beads surface-coated with avidin or streptavidin may be used. For example, commercially available products such as FluoroSpheres (Invitrogen) may be used.

A first protein conjugate 806 and a second protein conjugate 807 are obtained by separately immobilizing the first protein 801 and the second protein 802 to the charge carriers 804. The first protein conjugate 806 and the second protein conjugate 807 are then reacted to obtain a dimer 808.

The dimer 808 can be detected with high sensitivity with the method and the detection device of Embodiment 1 in the manner described therein, and the presence or absence of an interaction between the first protein 801 and the second protein 802 can be evaluated with high sensitivity.

The evaluation method also may be used as a method for conveniently screening whether a protein that interacts with a specific protein is contained in a specific library.

Embodiment 6

The configuration of the detection device of the present invention is described below with reference to FIG. 22.

A first solution tank 901 and a second solution tank 902 are separated from each other with a support 903. The detection device is disposed in contact with the first solution tank 901 situated above the support 903. The support 903 has a through hole (not shown), and the detection device is fixed to the support in contact therewith with the pore of the detection device in register with the through hole. Desirably, the through hole has a larger diameter than the pore, and the centers of the through hole and the pore are aligned. The support 903 is joined to a solution tank main body with a joint member 904.

The detection device is provided with wires (not shown) for measuring current changes between source and drain. Only one detection device or more than one detection device may be disposed on the support 903. In the case of providing more than one detection device, measurements can be simultaneously performed in parallel when the devices are adapted to individually measure the electrical signals between source and drain.

A sample solution containing an analyte is supplied into the first solution tank 901 from a sending unit 909 through a valve 908 and an inlet 906. The sending unit 909 includes means for mixing, reacting, and purifying sample biomolecules and antibody-attached charge carriers (not shown). For example, the mixing means may be one with a stirrer, or may be one that uses ultrasonic waves. Reaction may be performed at ordinary temperature, and is preferably performed with a temperature controller when the temperature needs to be maintained at 37 degrees. When magnetic microparticles are used as charge carriers, purification becomes easier when an external magnetic field is applied. When polymer microparticles, proteins, or nucleic acid molecules are used as charge carriers, purification requires a membrane, and preferably uses an aspirator. A sample solution is introduced into the first solution tank 901 as a mixture of a measurement sample and reagents.

A washing liquid is supplied into the second solution tank 902 from a washing liquid unit 910 through the valve 908 and the inlet 906. The washing liquid is used to wash the sample solution that has moved into the second solution tank 902 from the first solution tank 901 through the pore of the detection device. The sample and waste liquid discharge through the valve 908 and an outlet 907.

An electrode 905 is disposed in each solution tank, and the voltage generated in a voltage applicator 913 under the control of a PC 911 via a wire 916 is applied between the first solution tank 901 and the second solution tank 902 via the electrodes 905. Under the applied electric field, the dimers of the charge carriers contained in the sample solution in the first solution tank 901 are transported from the first solution tank 901 to the second solution tank 902 through the pore of the detection device disposed on the support 903. The electrical signals generated by the passage of the charge carriers through the pore of the detection device are sent to the PC 911 through a wire 914, and used for data processing.

The wire 914 is connected to the source and drain of the detection device, and the electrical signals generated by the passage of the charge carriers through the pore collect into the wire 914, and are sent to the PC 911. The difference in the electrical signals generated by the passage of dimers and monomers is identified and detected, and the number of times the dimers pass through the pore is counted to calculate the amount of the measurement target contained in the sample solution.

A control unit 912 controls the temperature and pH of the solution in the solution tanks under the control of the PC 911 via a wire 915. The detection device detects biomolecules with the foregoing configuration.

Embodiment 7

Another configuration of the detection method and device of the present invention is described below with reference to FIG. 23.

The method disclosed in this embodiment takes advantage of the physical size of charge carriers instead of charge amounts, and determines the abundance of biomolecules by detecting the presence of biomolecules through detection of a current change in the pore as it occurs when the dimer of charge carriers physically closes the pore during the passage of the biomolecule-linked charge carrier conjugate through the pore.

The dimer of charge carriers with the detection target biomolecule can be formed in the manner described in Embodiment 1.

A first solution tank 901 and a second solution tank 902 are separated from each other with a support 903. A pored thin film 917 is disposed in contact with the first solution tank 901 situated above the support 903. The support 903 has a through hole, and the thin film 917 is disposed with its pore in register with the through hole of the support 903.

The pore diameter is larger than the diameters of the charge carriers used, and is smaller than two times of the diameters of the charge carriers.

The film thickness is preferably no greater than two times the diameters of the charge carriers because it enables clearly distinguishing between the charge carrier conjugate and a simple charge carrier.

The support 903 is joined to the solution tank main body with a joint member 904.

A sample solution is supplied into the first solution tank 901 from a sending unit 909 through a valve 908 and an inlet 906. The sending unit 909 includes means for mixing, reacting, and purifying sample biomolecules and antibody-attached charge carriers (not shown). For example, the mixing means may be one with a stirrer, or may be one that uses ultrasonic waves. Reaction may be performed at ordinary temperature, and is preferably performed with a temperature controller when the temperature needs to be maintained at 37 degrees. When magnetic microparticles are used as charge carriers, purification becomes easier when an external magnetic field is applied. When polymer microparticles, proteins, or nucleic acid molecules are used as charge carriers, purification requires a membrane, and preferably uses an aspirator.

An electrolyte is dissolved in the sample solution in advance. For example, it is preferable to dissolve sodium chloride or potassium chloride in a concentration of 1 mM to 500 mM.

A washing liquid is supplied into the second solution tank 902 from a washing liquid unit 910 via the valve 908 and the inlet 906.

The sample solution and waste liquid discharge through the valve 908 and an outlet 907.

An electrode 905 is disposed in each solution tank, and the voltage generated in a voltage applicator 913 under the control of a PC 911 via a wire 916 is applied between the first solution tank 901 and the second solution tank 902 via the electrodes 905.

Under the applied electric field, the dimers of the sample charge carriers obtained in the manner described in Embodiment 1 are transported from the first solution tank 901 to the second solution tank 902 through the pore of the thin film 917 disposed on the support 903. The current passing between the first solution tank 901 and the second solution tank 902 is measured with an ammeter 918. The electrical signals from the ammeter 918 are sent to the PC 911 through a wire 919, and used for data processing. A control unit 912 controls the temperature and pH of the solution in the solution tanks under the control of the PC 911 via a wire 915.

The ammeter 918 measures the current that generates as the cations or anions of the electrolyte pass through the pore. The current value drops when the charge carrier physically closes the pore as it passes through the pore of the pored thin film 917. A reduction of the current value is dependent on the physical size of the charge carrier passing the pore. The amounts of current reduction thus become very different for monomeric charge carriers and dimeric charge carriers.

It is therefore possible to clearly identify the passage of a monomer or a dimer by measuring a reduction of the current value. Further, because the current reductions occur over time in the form of spikes, the number of dimers passing the pore can be accurately counted. The detection device can detect biomolecules with the foregoing method and configuration.

REFERENCE SIGNS LIST

101: Biomolecule
102: First antibody
103: Functional group
104: Second antibody
105: Sandwich conjugate
106: Unreactant
107: Charge carrier
108: Binding molecule
109: Dimer
110: Reaction product other than dimers
111: First solution tank
112: Second solution tank
113: Support
114: Detection device
115: Control gate
116: Source
117: Drain
118: Pore
119: Substrate
120: Reaction liquid flow
121: Channel
200: Insulating film
201: Channel
202: Control gate
203: Source
204: Drain
205: Backgate
206: Pore
207: Contact, wire
208: Si substrate
209: Silicon nitride film
210: Silicon nitride film
211: Polysilicon
212: Polysilicon
214: Pore
215: Pad
300: Pore disposed region
600: Semiconductor substrate chip
601: PC
602: Board
603: Chip with a pored sensor (a single sensor or an array of sensors) and a part of peripheral circuits
604: ADC and other signal processing circuits
605: Chip with a pored FET sensor (a single sensor or an array of small numbers of sensors), ADC, and other signal processing circuits
606: Chip of primarily a pored FET sensor (a single sensor or an array of small numbers of sensors)
607: ADC and peripheral signal processing circuit portion
608: ADC and peripheral signal processing circuit portion
701: Nucleic acid molecule
702: First functional group
703: Second functional group
704: Charge carrier
705: Charge carrier conjugate
706: Nucleic acid probe molecule
707: Dimer 708: Charge carrier
801: First protein
802: Second protein
803: Second functional group
804: Charge carrier
805: First functional group
806: First protein conjugate
807: Second protein conjugate
808: Dimer
901: First solution tank
902: Second solution tank
903: Support
904: Joint member
905: Electrode
906: Inlet
907: Outlet
908: Valve
909: Sending unit
910: Washing liquid unit
911: PC
912: Control unit
913: Voltage applicator
914: Wire
915: Wire
916: Wire
917: Pored thin film
918: Ammeter
919: Wire

The invention claimed is:

1. A biomolecule detection method comprising:

causing a reaction between a plurality of detection target biomolecules, a plurality of first antibodies against the biomolecule, and a plurality of second antibodies against the biomolecule to form a plurality of sandwich conjugates, and reacting the sandwich conjugates with a plurality of charge carriers to form a plurality of dimers, each of the dimers containing one of the sandwich conjugates and two of the charge carriers; and moving a reaction liquid containing the dimers and a reaction product other than dimers between a first flat surface and a second flat surface through a pore of a substrate, wherein the first flat surface of the substrate has a control gate and a channel, the pore penetrates through the substrate from the first flat surface to the second flat surface of the substrate, and the pore is located between the control gate and the channel; and counting the dimers passing through the pore by measuring amounts of current change in the channel to detect the presence of the biomolecules.

2. The biomolecule detection method according to claim 1, wherein the substrate has a field-effect transistor disposed on the first flat surface that includes an insulating film, the control gate, a source and a drain separated by the channel, wherein the control gate exhibits an electric field effect on the channel, and wherein an amount of the counted dimers correspond to an abundance of the biomolecules.

3. The biomolecule detection method according to claim 1, wherein the substrate separates a first solution tank on a side of the first flat surface and a second solution tank on a side of the second flat surface.

4. The biomolecule detection method according to claim 3, wherein the pore has a diameter that is larger than a diameter of the charge carriers, and that is no larger than two times the diameter of the charge carriers, and wherein the substrate has a thickness that is no greater than two times the diameter of the charge carriers.

5. The biomolecule detection method according to claim 1, wherein the charge carriers are at least one of magnetic microparticles, polymer microparticles, proteins, and nucleic acids.

* * * * *